US012632260B2

(12) United States Patent
Kilbey et al.

(10) Patent No.: US 12,632,260 B2
(45) Date of Patent: **\*May 19, 2026**

(54) HIP ORTHOTIC WITH A REMOVABLE RIGID BRACE ASSEMBLY

(71) Applicants: Bryan E Kilbey, DeFuniak Springs, FL (US); Geoffrey Van Thiel, DeFuniak Springs, FL (US); Ajay Lall, DeFuniak Springs, FL (US)

(72) Inventors: Bryan E Kilbey, DeFuniak Springs, FL (US); Geoffrey Van Thiel, DeFuniak Springs, FL (US); Ajay Lall, DeFuniak Springs, FL (US)

( \* ) Notice: Subject to any disclaimer, the term of this patent is extended or adjusted under 35 U.S.C. 154(b) by 116 days.

This patent is subject to a terminal disclaimer.

(21) Appl. No.: 18/214,778

(22) Filed: Jun. 27, 2023

(65) Prior Publication Data

US 2023/0342155 A1 Oct. 26, 2023

Related U.S. Application Data

(63) Continuation of application No. 16/675,212, filed on Nov. 5, 2019, now Pat. No. 11,144,322.

(51) Int. Cl.
| | |
|---|---|
| *G06F 9/38* | (2018.01) |
| *A61F 5/01* | (2006.01) |
| *A61F 7/00* | (2006.01) |
| *A61F 7/02* | (2006.01) |
| *G06F 3/06* | (2006.01) |
| *G06F 9/30* | (2018.01) |
| *G06F 9/54* | (2006.01) |
| *G06F 12/02* | (2006.01) |
| *G06F 15/173* | (2006.01) |

(52) U.S. Cl.
CPC .......... *G06F 9/3836* (2013.01); *A61F 5/0102* (2013.01); *A61F 5/0193* (2013.01); *A61F 7/00* (2013.01); *A61F 2005/0148* (2013.01); *A61F 2005/0158* (2013.01); *A61F 2005/0165* (2013.01); *A61F 2007/004* (2013.01); *A61F 2007/0244* (2013.01); *G06F 9/3004* (2013.01)

(58) Field of Classification Search
CPC ........ A61F 5/01; A61F 5/0102; A61F 5/0104; A61F 5/0123; A61F 5/0125; A61F 5/0193; A61F 5/026; A61F 5/028; A61F 5/3715; A61F 2007/004; A61F 2007/0041; A61F 2005/0132; A61F 2005/0183; A61H 1/0237; A61H 1/0244; A61H 1/0255; A61G 13/123
See application file for complete search history.

(56) References Cited

U.S. PATENT DOCUMENTS

| | | | | |
|---|---|---|---|---|
| 11,684,504 B2 * | 6/2023 | Kilbey | ................. | A61F 5/0193 602/13 |
| 2005/0283102 A1 * | 12/2005 | Schwenn | .............. | A61F 5/0193 602/5 |
| 2017/0216076 A1 * | 8/2017 | Turconi | ................... | A61F 7/00 |

\* cited by examiner

*Primary Examiner* — Alireza Nia
*Assistant Examiner* — Andrew Jun-Wai Mok
(74) *Attorney, Agent, or Firm* — J. Wiley Horton

(57) ABSTRACT

A hip joint orthotic that can be used in stages. In the first stage the orthotic includes a stiff relatively brace assembly that can limit the amount of allowed flexion, extension, abduction, and adduction. In the second stage the relatively stiff brace can be removed and the orthotic can be used as a soft wrap. In both stages the orthotic is configured to easily mount and retain a thermal pack in a desired position or positions. In many instances the thermal pack will be a cold pack, but in some cases a hot pack may be used as well.

11 Claims, 26 Drawing Sheets

HIP ORTHOTIC WITH A REMOVABLE RIGID BRACE ASSEMBLY

CROSS-REFERENCES TO RELATED APPLICATIONS

This application is a continuation of pending U.S. patent application Ser. No. 16/657,212 (U.S. Pat. No. 11,684,504). The parent application was filed on Oct. 18, 2019.

STATEMENT REGARDING FEDERALLY SPONSORED RESEARCH OR DEVELOPMENT

Not Applicable

Microfiche Appendix

Not Applicable

BACKGROUND OF THE INVENTION

1. Field of the Invention

This invention relates to the field of medical products. More specifically, the invention comprises a hip brace that is configured to position and retain thermal transfer packs, among other things.

2. Description of the Related Art

Hip replacement surgery is often an open procedure requiring a relatively large incision. Significant tissue displacement is required during the preparation and insertion of an artificial joint. In recent years arthroscopic hip surgery has become increasingly common, and this has reduced the wound size and tissue disruption. Whether an open or closed procedure, it is generally important after such a surgery to control the motion of the hip joint. It is also desirable in many instances to provide cold therapy in order to reduce inflammation. The present invention addresses both these concerns as well as additional concerns.

BRIEF SUMMARY OF THE PRESENT INVENTION

The present invention provides a hip joint orthotic that can be used in stages. In the first stage the orthotic includes a relatively stiff brace assembly that can limit the amount of allowed flexion, extension, abduction, and adduction of the hip joint. In the second stage the relatively stiff brace can be removed and the orthotic can be used as a soft wrap. In both stages the orthotic is configured to easily mount and retain a thermal pack in a desired position or positions. In many instances the thermal pack will be a cold pack, but in some cases a hot pack may be used as well.

REFERENCE NUMERALS IN THE DRAWINGS

Figure 1:
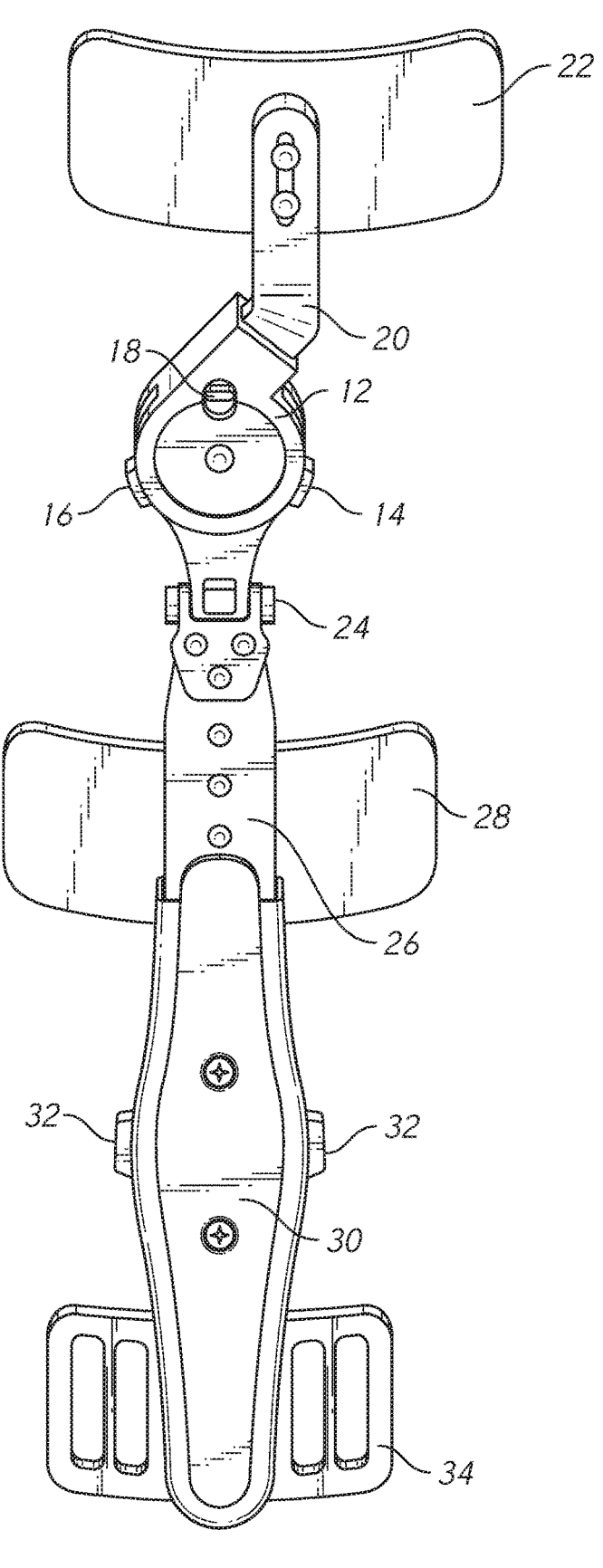
FIG. 1 is a perspective view showing the brace assembly used in the present invention.

10 brace assembly
12 pivot mechanism
14 flexion stop
16 extension stop
18 lock
20 upper link
22 upper plate
24 abduction pivot
26 lower link
28 lower plate
30 slide body
32 slide release
34 thigh belt plate
36 upper plate cover
38 waist panel 40 thigh panel
42 waist strap
44 upper thigh strap
46 lower thigh strap
48 soft backing
50 belt buckle
52 central web
54 sheave assembly
56 adjustment tab
57 adjustment tab
58 cord
60 sheave body
62 groove
64 coupler
66 user
68 receiver
70 release button
72 hook panel
73 hook panel
74 adjustable coupling
80 leg
82 pocket
84 hook panel
86 removed length
87 tang
88 hook panel
90 thermal pack
91 pneumatic panel assembly
92 sealed perimeter
93 squeeze bulb
94 hook panel
95 release
96 air valve
97 adjustable coupling
98 hook tab
100 edge band
102 seam
104 air bladder
106 outer layer
110 anchor plate
112 sheave body
114 center section
116 slot
120 frame
122 cord anchor
124 cord anchor
126 slot
128 slide rivet
130 lower link
132 upper link
134 fastener
136 captive nut
138 hole
140 offset bracket
142 grip disk
144 insert
146 contact pad
148 hook panel
150 hook panel
152 hook panel
154 hook panel
156 relief
158 notch
160 prong
162 hole
164 polymer lower plate
166 retaining ring 168 insert
170 captive nut

DETAILED DESCRIPTION OF THE INVENTION

Figure 2:
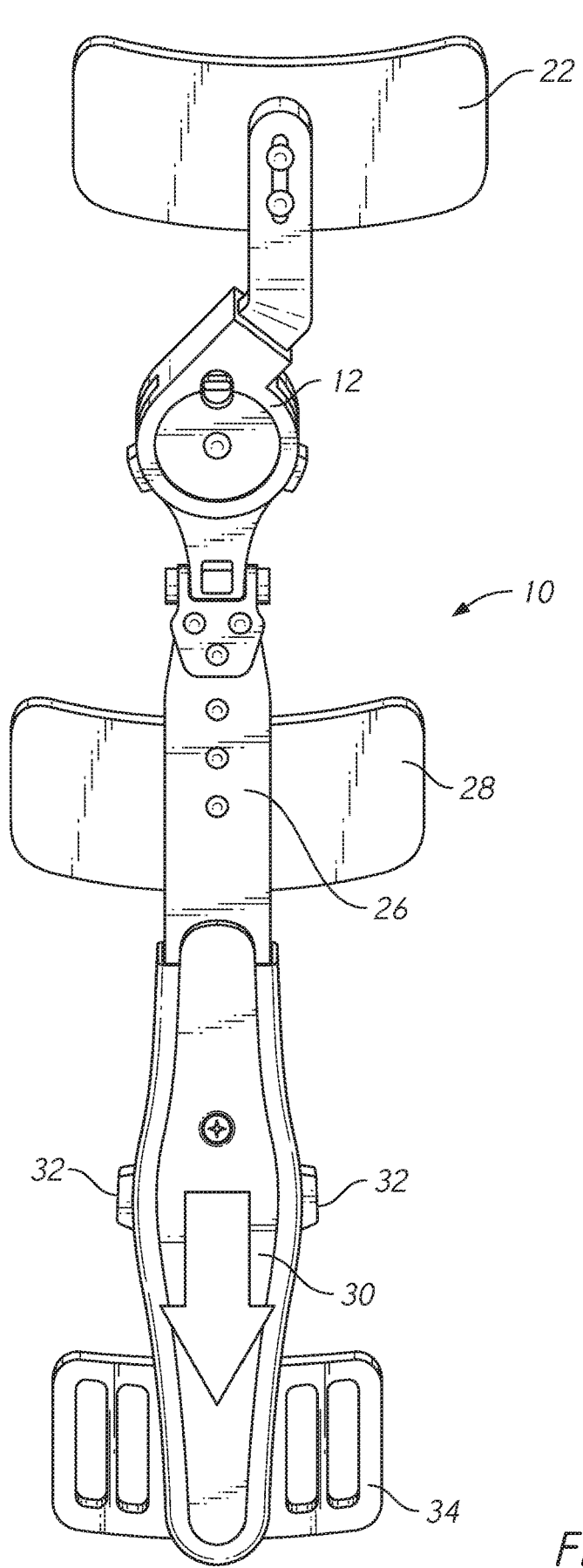
FIG. 2 is a perspective view, showing the operation of the slide body used in the brace assembly of FIG. 1.

The inventive orthotic includes a rigid brace assembly, a flexible panel assembly, and several belts and adjustment devices. FIGS. 1-3 depict brace assembly 10. Upper link 20 is connected to lower link 26 by pivot mechanism 12. Upper link 20 is intended to run roughly parallel to the user's torso while lower link 26 is intended to run roughly parallel to the user's thigh.

Upper plate 22 is connected to the upper portion of upper link 20. The upper plate is preferably curved to conform to the user's lateral pelvic area. Lower plate 28 is connected to lower link 26. The lower plate is preferably curved to conform to the user's outer thigh. Both the upper and lower plates may be made of soft metal so that a technician can adjust their curvature to suit a particular individual.

Pivot mechanism 12 may be a variety of mechanisms that are known in the field. In the version show, lock 18 can be set to eliminate any pivoting motion between the upper and lower link. Flexion stop 14 and extension stop 16 can be moved to a desired position in order to limit the flexion or extension of the hip joint.

Abduction pivot 24 is provided to allow the hip to move in abduction over a small range. Slide body 30 slides up and down along lower link 26 in order to reposition thigh belt plate 34 and the thigh belt that is attached thereto. FIG. 2 shows this feature in motion. In the version shown the user presses inward on a pair of slide releases 32 and moves slide body 30 downward while holding the slide releases in. Once the slide body reaches the desired position the user allows the two slide releases to pop outward and this action then locks the slide body in place. Many different locking mechanisms can be used to allow and restrain the motion of the slide body.

Figure 3A:
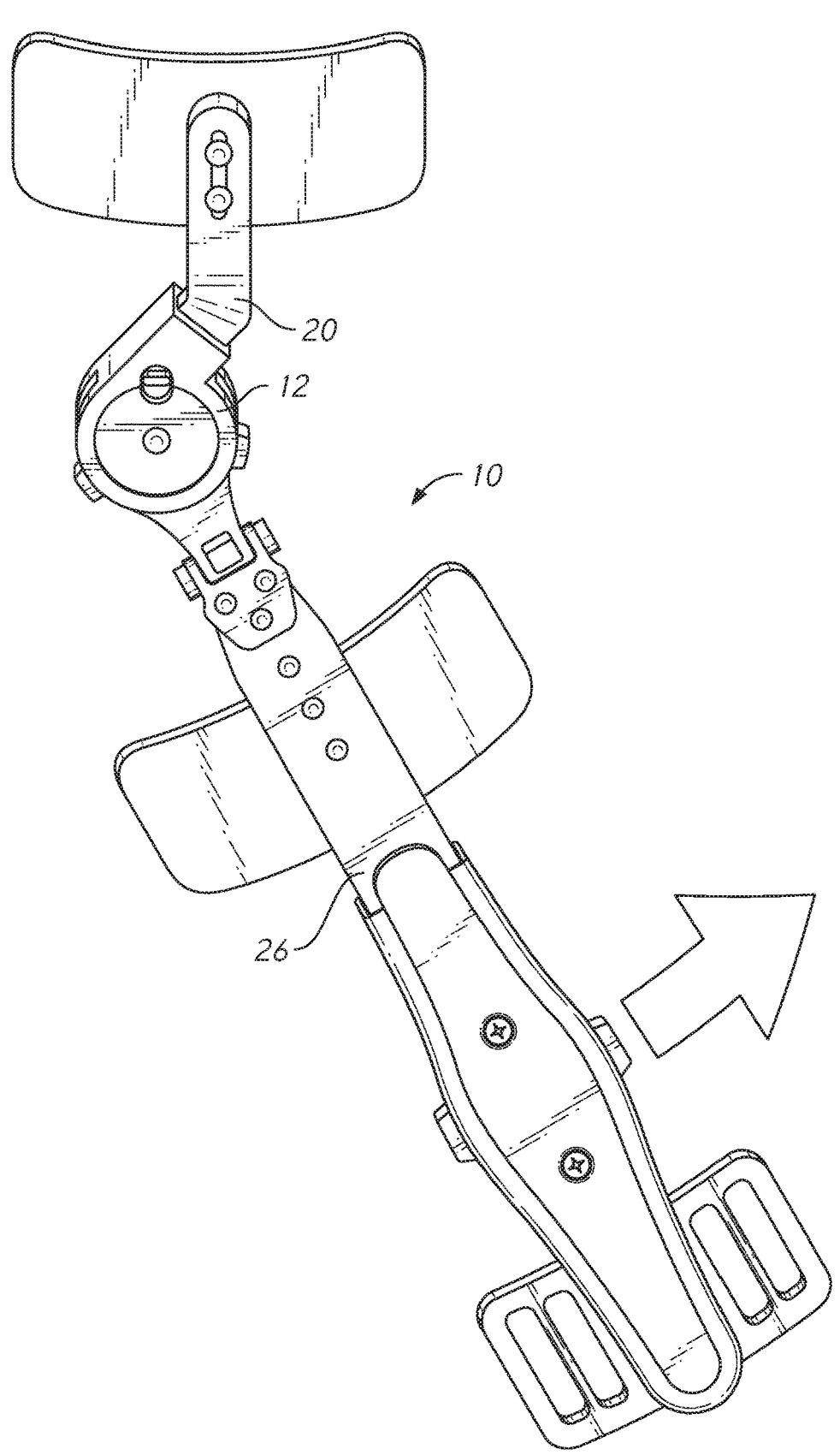
FIG. 3A is a perspective view, showing the operation of the pivot mechanism in the brace assembly.

FIG. 3A shows the brace assembly with pivot mechanism 12 in an unlocked state. Lower link 26 is free to pivot with respect to upper link 20. The range of available motion can be set by the flexion and extension limits described previously.

Figure 3B:
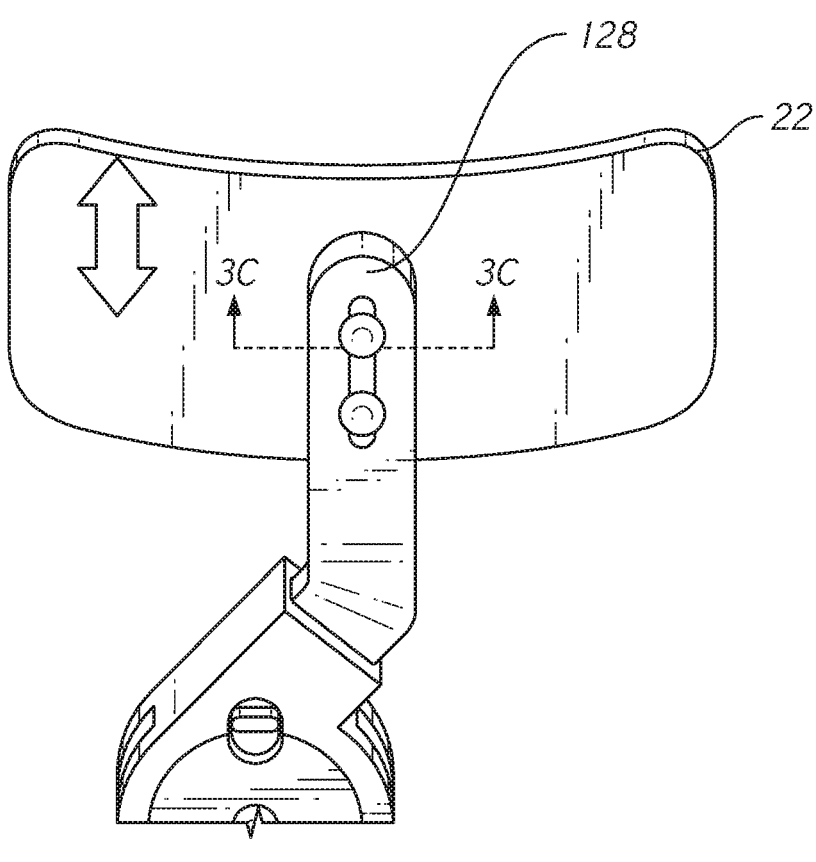
FIG. 3B is a perspective view, showing the operation of a slide joint between the upper link and the upper plate
Figure 3C:
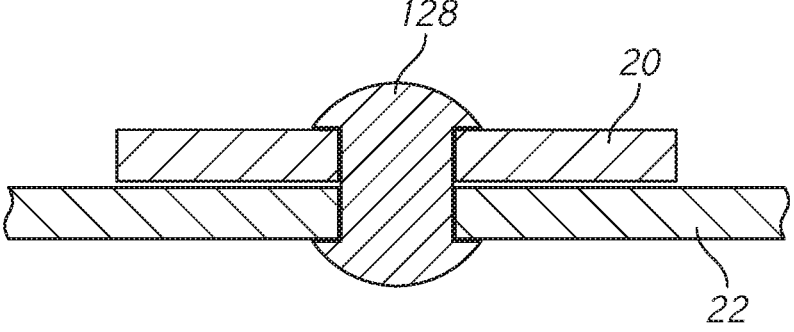
FIG. 3C is a sectional view, showing the operation of the sliding joint between the upper link and the upper plate.

FIGS. 3B and 3C show an embodiment in which an additional degree of freedom is provided between upper link 20 and upper plate 22. A vertical slot 126 is provided in the upper portion of upper link 20. Two slide rivets 128 are connected to upper plate 22. These slide rivet (which may assume various forms) move with upper plate 22 but slide freely within slot 126. FIG. 3C provides a section view through these components. The reader will note how slide rivets 128 connect upper link 20 and upper plate 22, but allow the upper plate to slide freely over the upper link (subject to the upper and lower boundaries of the slot. Multi-component fasteners may be substituted for the simplistic slide rivets shown.

Returning now to FIG. 3B, the reader will understand that upper plate 22 is free to slide up and down with respect to upper link 20—subject to the limits of slot 126. This feature allows the inventive orthotic to be more comfortable when a user takes a sitting position—as will be described subsequently.

Figure 4:
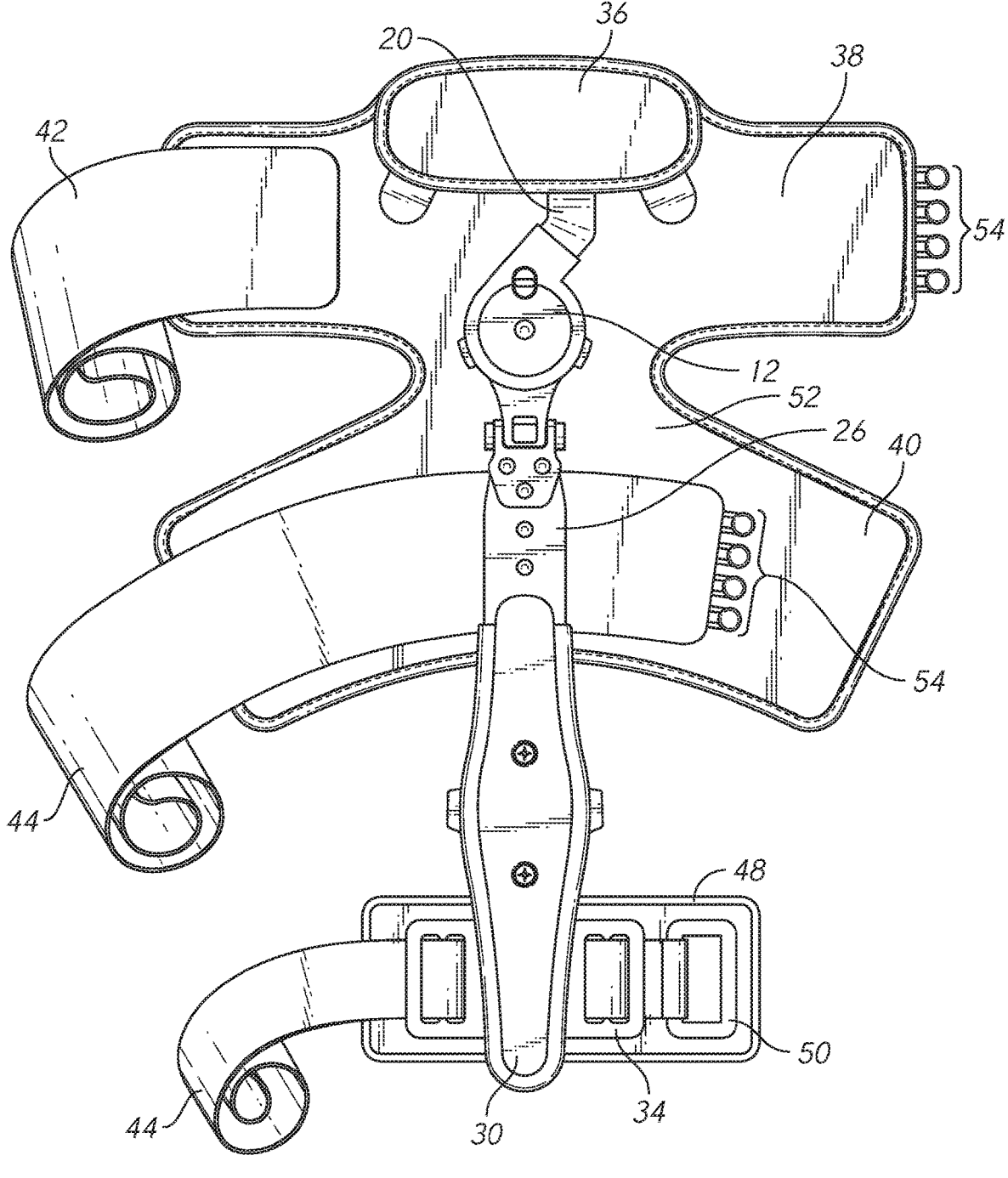
FIG. 4 is a perspective view, showing the union of the brace assembly and the panel assembly.

FIG. 4 shows the brace assembly, the panel assembly, and other components assembled to form an example of the inventive orthotic. The panel assembly includes waist panel 38, thigh panel 40, and central web 52 (which links the waist panel and the thigh panel). Pivot mechanism 12 lies roughly over the location of central web 52. Upper link lies over the center of waist panel 38 (with the upper plate of the upper link lying under upper plate cover 36). Lower link 26 lies primarily over thigh panel 40.

Waist strap 42 has a first end secured to the left portion of waist panel 38 ("left" being understood with respect to the orientation shown in FIG. 4). A second end of the waist strap is free. Upper thigh strap 44 extends across most of thigh panel 40. A first end of the upper thigh strap is secured to lower link 26 and a second end of the upper thigh strap is free.

Thigh belt plate 34 is connected to the lower end of slide body 30. Soft backing 48 lies beneath the thigh belt plate and prevents discomfort for the user. Lower thigh strap 46 is engaged through loops in the thigh belt plate. In the version shown, belt buckle 50 is provided on a first end of the lower thigh belt while the second end of the belt is free.

Two sheave assemblies 54 are shown in FIG. 4. These form part of an adjustment mechanism for closing and adjusting the length of the waist strap and the upper thigh strap. The upper sheave assembly 54 is preferably sewn or otherwise connected to waist panel 38. The lower sheave assembly 54 is preferably sewn or otherwise connected to one end of upper thigh strap 44.

Figure 5:
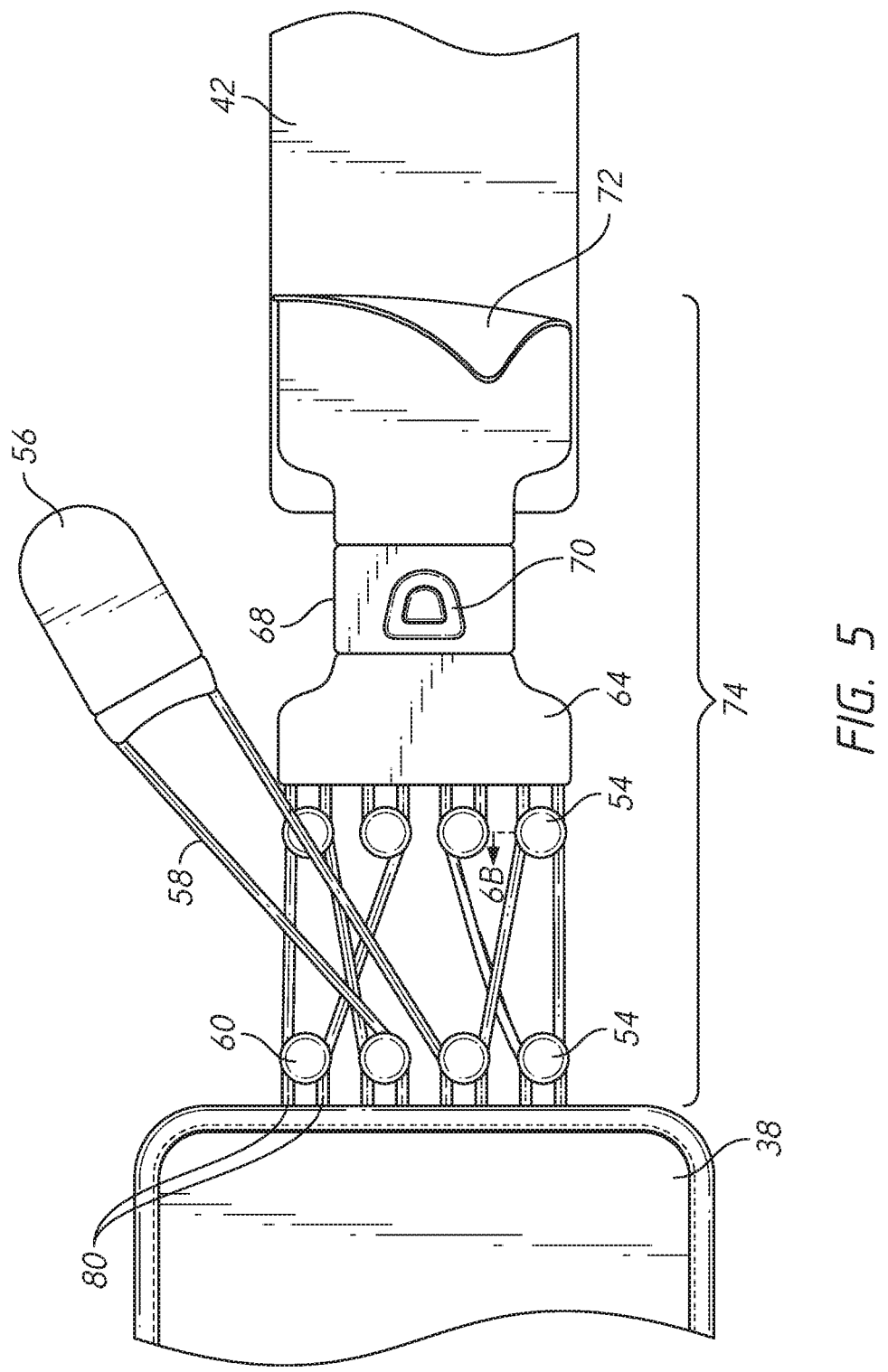
FIG. 5 is a detailed view, showing an adjustable coupling.
Figure 6A:
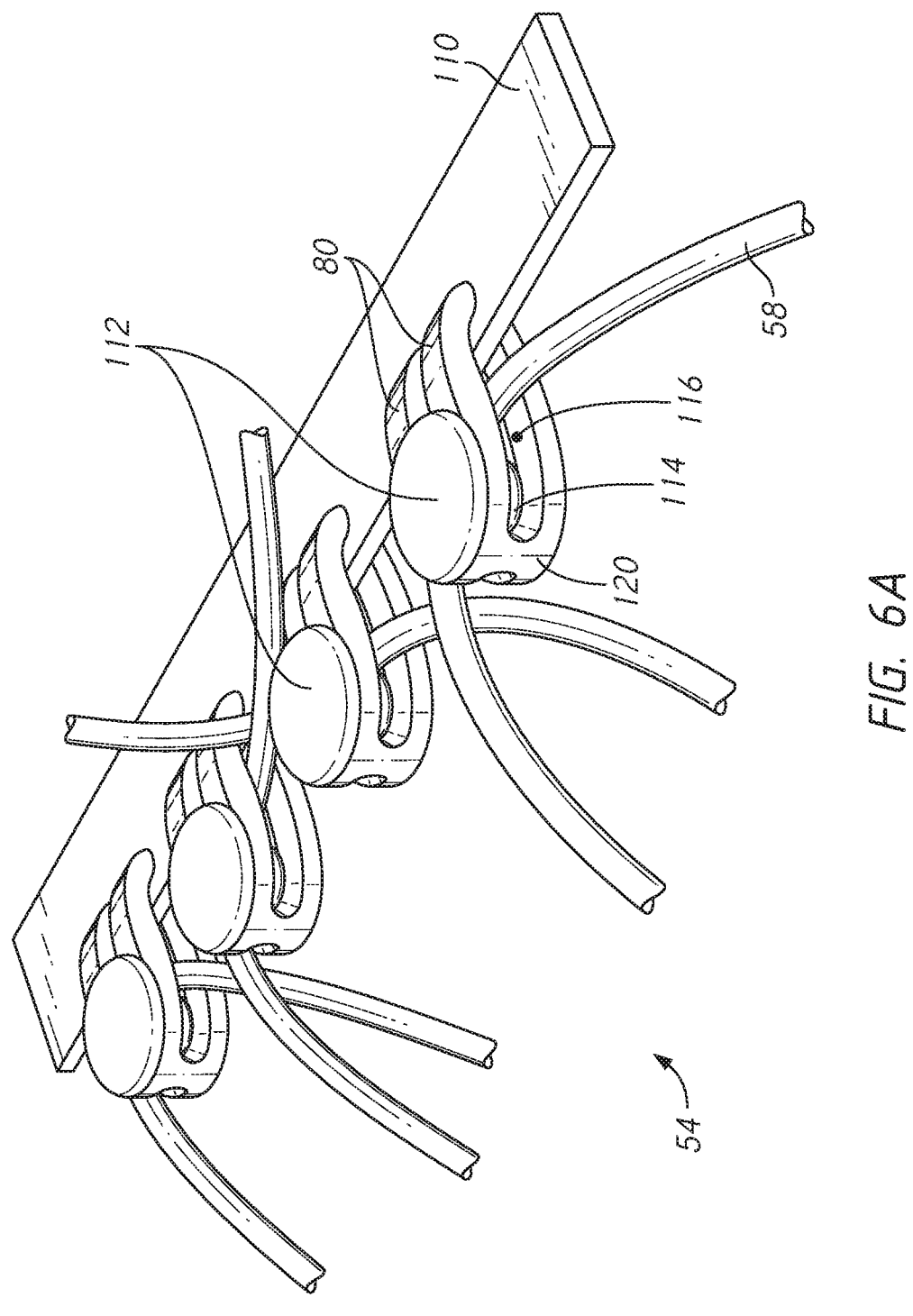
FIG. 6A is a perspective view showing a sheave assembly.
Figure 6B:
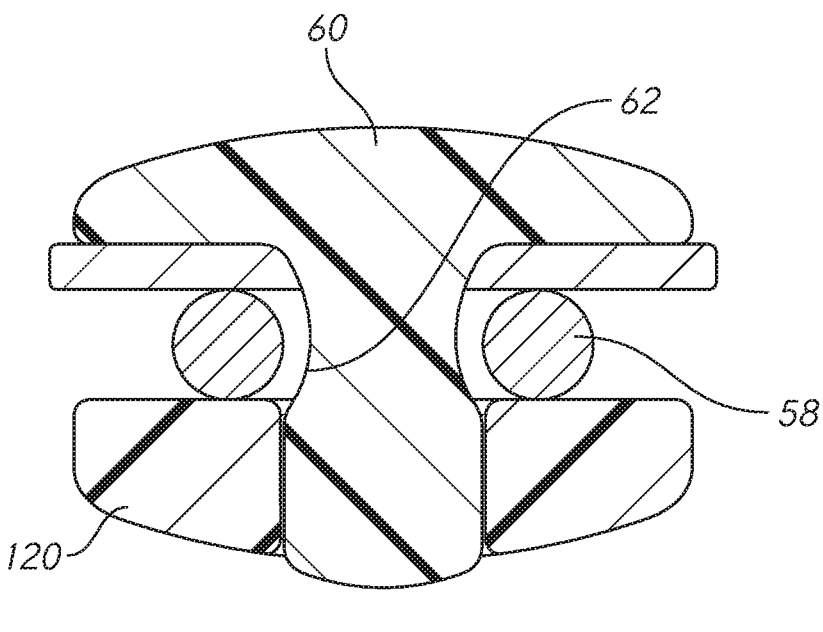
FIG. 6B is a sectional elevation view through one of the sheave bodies shown in FIG. 5.

FIGS. 5, 6A, and 6B show additional details regarding the sheave assemblies and the adjustment mechanisms they form part of FIG. 5 shows a detail view of adjustable coupling 74 as applied to waist strap 42. The sheave assembly 54 on the left side of the view is attached to waist panel 38. A second sheave assembly 54 is attached to (or molded as part of) coupler 64. In this example each sheave assembly 54 includes four separate sheaves 60.

Coupler 64 is releasably connected to receiver 68. Receiver 68 is connected to hook panel 72. Hook panel 72 is connected at a desired position to the outward facing surface of the free end of waist strap 42. The outward facing surface of the waist strap is covered with loop material (Throughout this disclosure the term "loop material" is intended to mean a material that can receive and engage a hook panel. Those skilled in the art will know that many modern loop materials are smooth and the fact that they are hook-compatible is not immediately obvious. Modern loop materials are often not "fuzzy" like the loop materials of past years). The inward facing surface of hook panel 72 is covered in hook material, so that hook panel 72 will stick to the outward facing surface of the waist strap wherever it is pressed into position.

FIG. 6A shows a detailed view of a sheave assembly 54. Each individual sheave includes a sheave body 112 in a corresponding frame 120. In the example shown each frame 120 has four connecting legs 80. Each sheave body 112 also includes a center section 114 that passes across a slot 116. Cord 58 passes through slot 116 and around center section 114. Each sheave body thereby acts like a pulley. It is not necessary for the sheave bodies to actually rotate in the frames. As long as center section 114 is a relatively low-friction material cord 58 can slide easily through as the device is adjusted.

In the example shown frames 120 and anchor plate 110 are molded as one integral piece of plastic. Each sheave body 112 is pressed into position in a corresponding relief in a frame 120. Anchor plate 110 is preferably made thin enough so that a heavy gauge needle can pass through it and sew it to a portion of a belt or the panel assembly. Alternatively, the sheave assembly can be molded as part of a larger molded clasp or other feature.

FIG. 6B shows a section through one of the sheave bodies and frames. Groove 62 is preferably incorporated into center section 114. This groove helps to control the location of cord 58 as it passes around the center section.

Returning now to FIG. 5 the operation of the adjustment mechanism will be explained. The reader will observe that the two sheave assemblies 54 oppose each other across a gap. Cord 58 is one continuous piece with two free ends. The first free end of the cord is secured to coupler 64 at cord anchor 122. The second free end is secured to coupler 64 at cord anchor 124. Adjustment tab 56 includes a hollow transverse passage and cord 58 passes through this as shown. The adjustment tab is preferably able to slide freely along the cord.

The cord is able to slide freely through each of the sheave bodies. The assembly shown operates like a block-and-tackle. If the user pulls adjustment tab 56 toward the right the two sheave assemblies 54 are pulled closer together with a considerable mechanical advantage. Adjustment tab 56 includes hook material on its inward facing surface. The outward facing side of hook panel 72 and waist strap 42 are covered in loop material. Once the desired level of tension for the waist strap is obtained by pulling the adjustment tab, the user presses the adjustment tab against the hook panel and/or waist strap and the hook and loop engagement secures the adjustment tab in position.

The embodiment depicted in FIG. 5 includes an additional helpful feature. Coupler 64 can be selectively disengaged from receiver 68 by pressing release button 70. The coupler can be reconnected to the receiver by sliding the two components together. When first donning the orthotic adjustment tab 56 can be left dangling. The user first connects the belt by snapping coupler 64 into receiver 68. The user then adds the desired level of tension by pulling adjustment tab 56 to the right and securing it in place.

Figure 7:
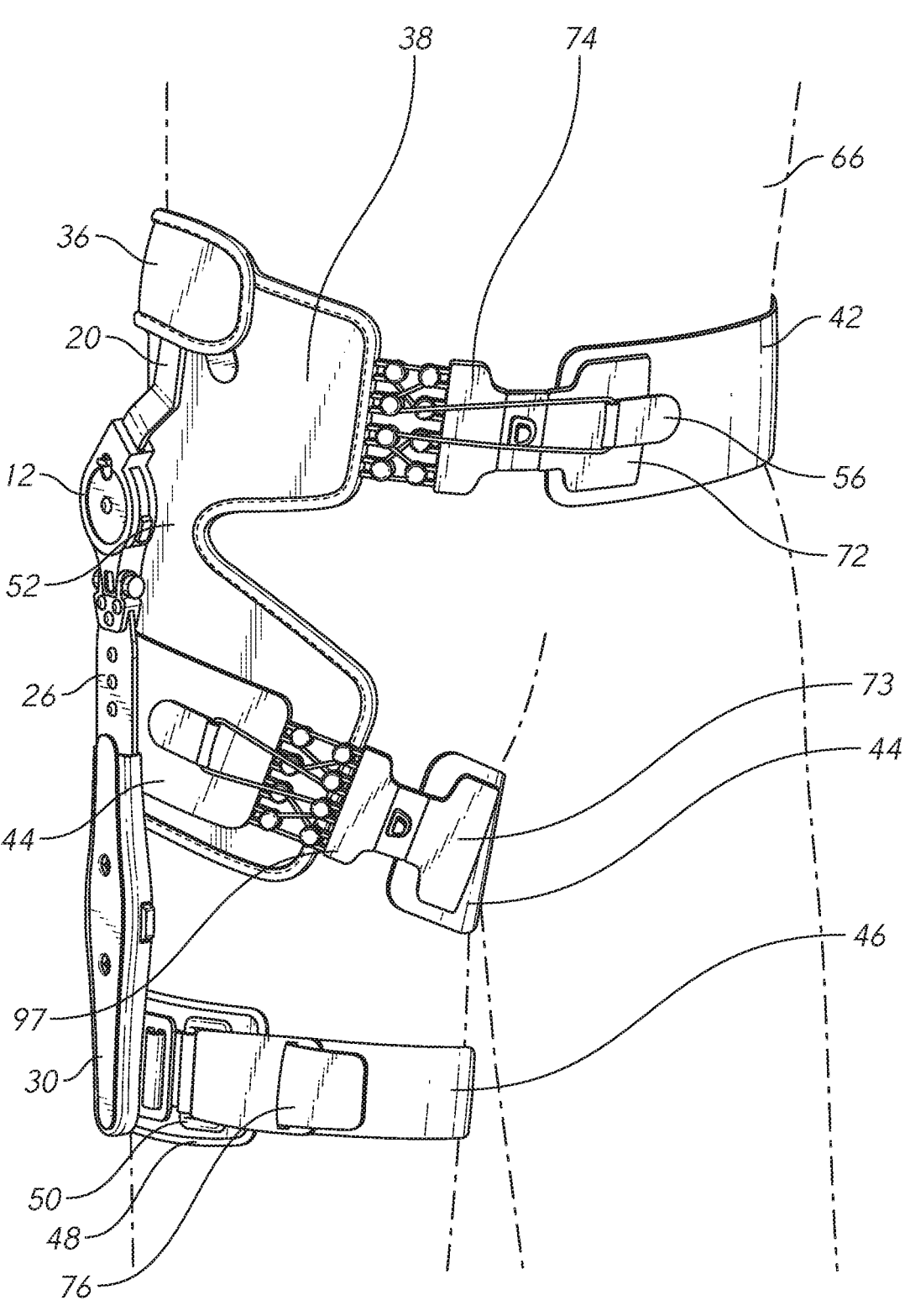
FIG. 7 is a perspective view, showing the invention installed on a user.

FIG. 7 shows the inventive orthotic installed on user 66. Waist strap 42 is passed around the user's waist and secured using adjustable coupling 74. Upper thigh strap 44 is passed around the user's upper thigh and secured using adjustable coupling 97. Slide body 30 is extended to the desired position and lower thigh strap 46 is then passed around the user's lower thigh. The lower thigh strap preferably includes loop covering on its inward and outward facing surfaces. This strap is passed through belt buckle 50. Hook panel 76 is then pressed over the end of the belt and back on the body of the belt to secure it in position as shown.

Adjustment tab 56 is lifted and moved to adjust the desired tension of waist strap 42. Adjustment tab 57 is lifted and moved to adjust the desired tension of upper thigh strap 44. A relatively low tension is applied with the position of adjustable tab 57 shown in FIG. 7. In many instances the user will pull the adjustment tab over lower link 26 and attach it posteriorly to lower link 26. Hook panel 76 is lifted and moved to adjust the desired tension of lower thigh strap 46.

The reader will note that pivot mechanism 12 is placed in line with the flexion/extension axis of the hip joint. The thin central web 52 of the panel assembly allows the panel assembly to bend with the pivot mechanism when the hip joint is flexed. This allows the desired post-surgical adjustment of the range of motion while also providing desired stability.

The reader will recall from FIG. 3B that in some embodiments of the present invention upper plate 22 is free to move up and down with respect to upper link 20. When a user goes from a standing position (such as shown in FIG. 7) to a sitting position the distance between the waist strap 42 and upper portion of waist panel 38 and pivot mechanism 12 will be shortened. Absent some accommodation for this phenomenon, the waist strap and upper portion of the panel assembly will assume an odd angle on the user and will become uncomfortable. The telescoping relationship between upper plate 22 and upper link 20 accommodates this variation by allowing upper plate 22 to move downward with respect to upper link 20 when the user sits. When the user again stands upper plate 22 will move back to its normal position with respect to the upper link (as shown in FIG. 7).

Figure 8:
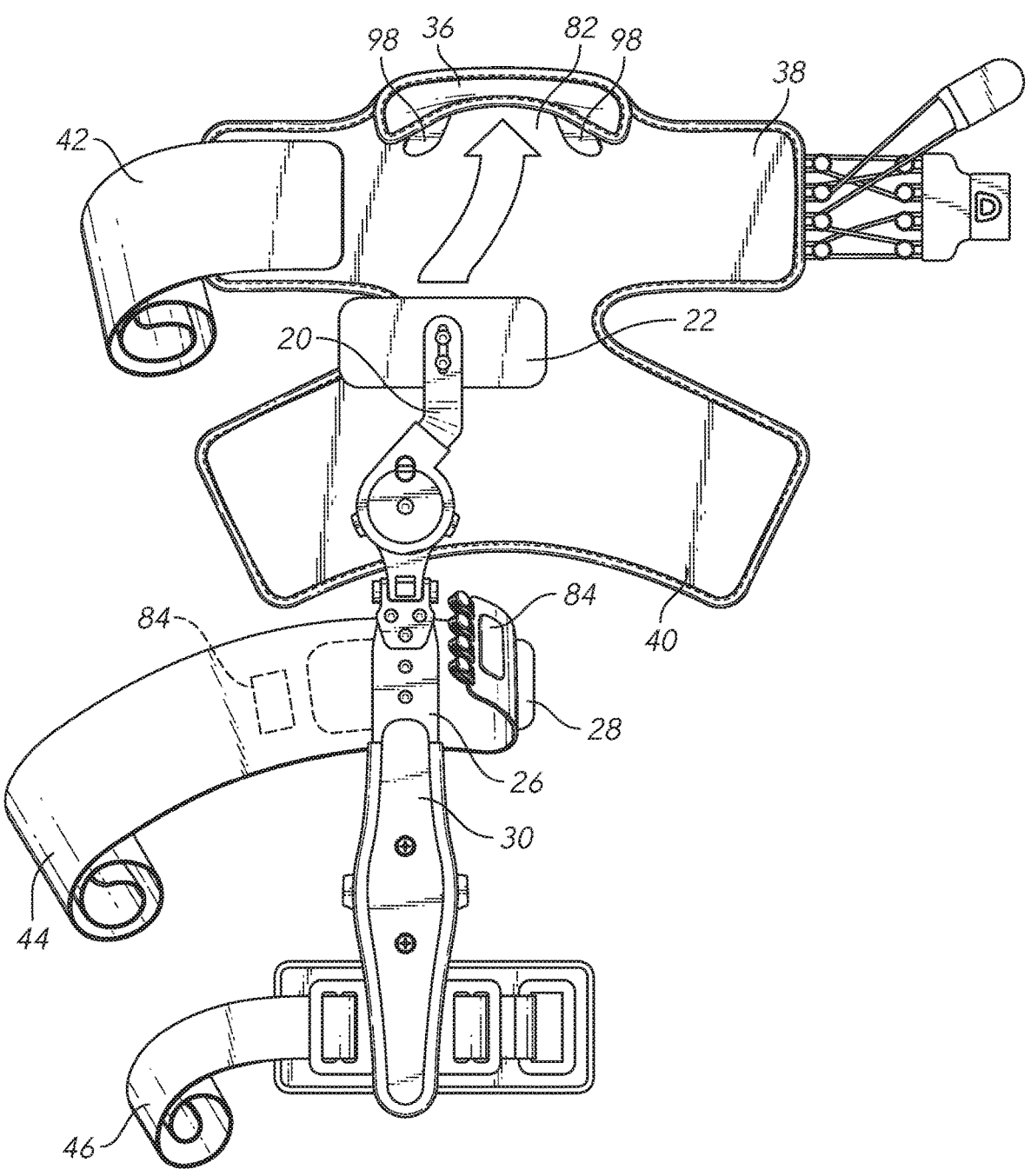
FIG. 8 is a perspective view, showing how the brace assembly and the panel assembly are united in a particular embodiment.

FIG. 8 illustrates one process for the assembly of the inventive orthotic. Upper plate cover 36 is sewn to waist panel 38 around three edges but the bottom edge remains open to form pocket 82. Upper plate 22 slides into pocket 82 as indicated by the arrow. The outward facing surface of waist panel 38 (the side facing the viewer in FIG. 8) is covered in loop material. Two hook tabs 98 are provided with inward facing hook panels. Once upper plate 22 is secure within pocket 82, the two hook tabs 98 are pressed against waist panel 38, thereby securing the upper plate within the pocket. Additional hook panels are preferably placed on the inward facing side of upper plate 22 (such as by using a high-bond adhesive tape). These additional hook panels directly engage the loop material on waist panel 38.

Upper thigh strap 44 is secured to lower link 26 by any suitable method. The attachment could be made by rivets, by stitching, by adhesive, or by releasable plastic connectors. It is preferable for upper thigh strap 44 to be removable from lower link 26 for reasons which will be described subsequently.

Upper thigh strap 44 is positioned to overlie lower plate 28 as shown. The upper thigh strap also includes a pair of hook panels 84 (one positioned just outside each of the two lateral extremes of the lower plate). The outward facing surfaces of the panel assembly are preferably all covered in loop material (waist panel 38, central web 52 and thigh panel 40). Once the brace assembly is in position, the user pushes the central portion of upper thigh belt 44 down against the panel assembly—causing the two hook panels 84 to engage. This—in conjunction with the upper plate being held within pocket 82—effectively locks the brace assembly to the panel assembly. The reader should note that most of adjustable coupling 97 is omitted in FIG. 8 for purposes of visual clarity. FIG. 4 shows the invention in an assembled state.

Figure 9:
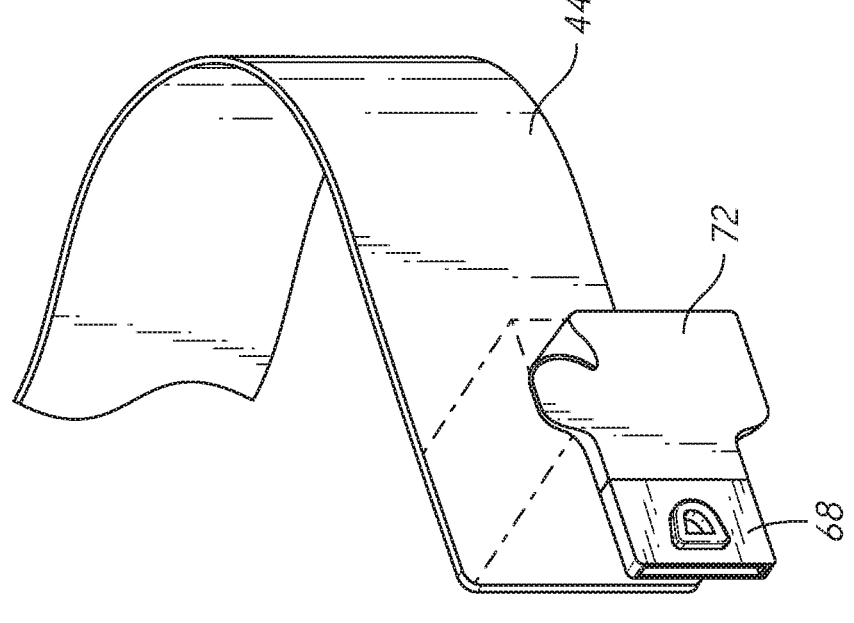
FIG. 9 is a perspective view, showing how the upper thigh strap can be cut to length.
Figure 9:
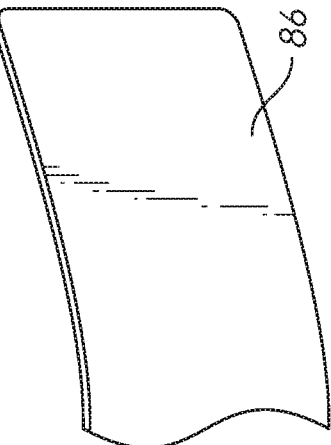

It is preferable for all the straps employed to be adjustable in length over a wide range. One option is to provide straps that can be trimmed to length. FIG. 9 shows a configuration allowing this. The length of upper thigh strap 44 is shortened by cutting away removed length 86. Hook panel 72 (which is attached to receiver 68) is then pressed into position on the outward facing surface near the newly formed end of upper thigh strap 44. The same operation can be performed for the waist strap.

Figure 11:
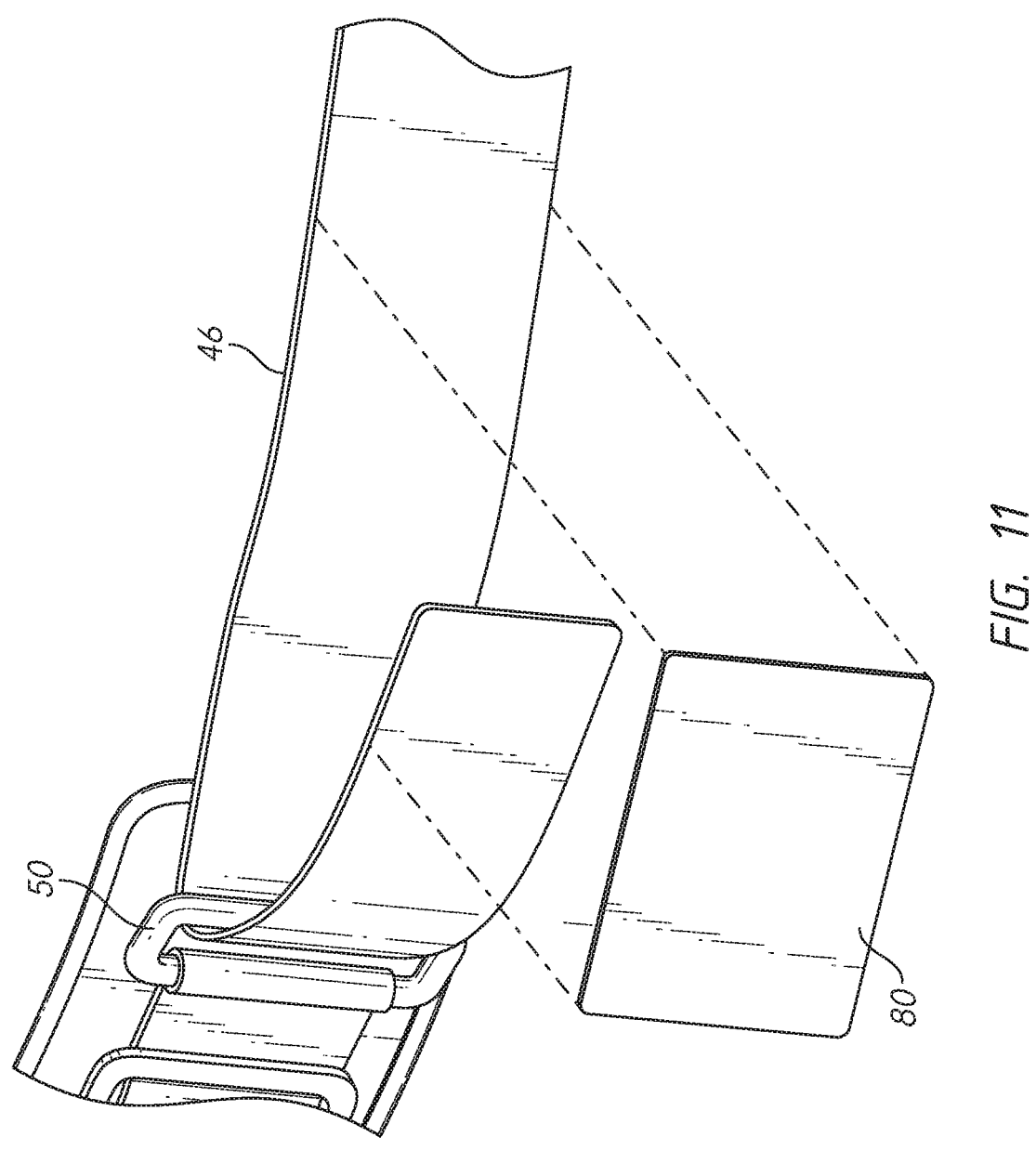
FIG. 11 is a perspective view, showing how the lower thigh strap can be cut to length.

FIG. 11 shows an even simpler operation that can be used for lower thigh strap 46. The thigh strap is equipped with loop material on both its inward and outward facing surfaces. The lower thigh strap 46 is passed through belt buckle 50 and drawn to the desired position. Any excess length is then cut free. The inward facing surface of hook panel 88 includes hook material. The hook panel is pressed into place as shown, with approximately half of the hook panel covering the free end of the lower thigh strap and half covering the body of the thigh strap. Once pressed into place, hook panel 88 secures the desired tension. However, hook panel 88 is easily removed in order to release the lower thigh strap.

Figure 10:
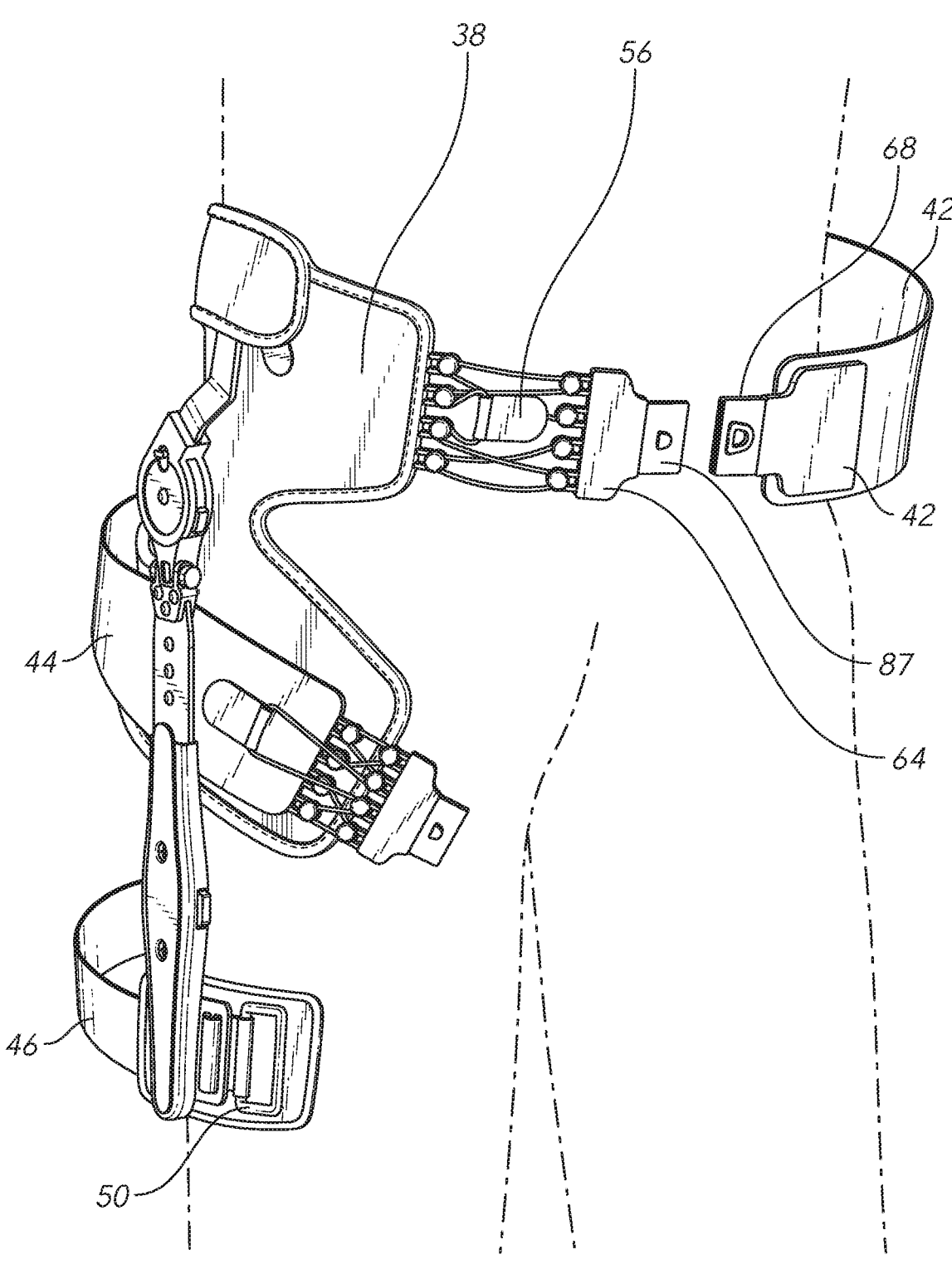
FIG. 10 is a perspective view, showing a user putting on the inventive orthotic.

FIG. 10 shows the customary first stage in applying the inventive orthotic. Waist panel 38 is placed proximate the affected hip and waist strap 42 is passed around the user's waist. Tang 87 on coupler 64 slides into receiver 68 where it snaps into place. The user may then place a desired amount of tension on the waist strap using tab 56.

The same process is repeated for upper thigh strap 44. The user secures lower thigh strap 46 by passing its free end through belt buckle 50 and then securing the lower thigh strap back on itself (using a hook panel) as described previously. The result is shown in FIG. 7. The user is able to individually adjust the tension on the waist strap, upper thigh strap, and lower thigh strap by moving adjustment tab 56, adjustment tab 57, and hook panel 76 (respectively).

Figure 12:
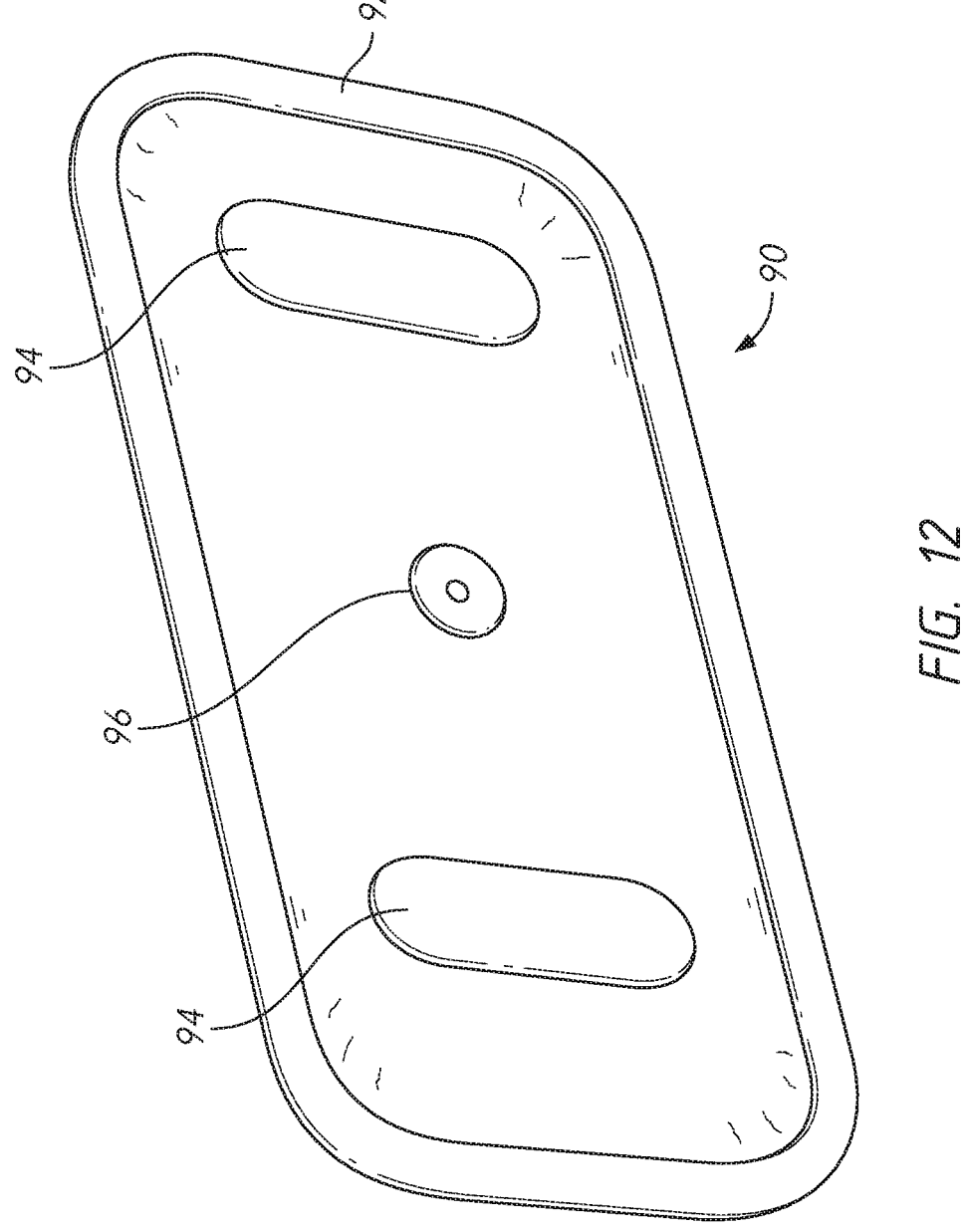
FIG. 12 is a perspective view, showing a thermal pack configured for use in the present invention.

An important advantage of the present invention is its ability to secure a thermal pack or packs against the body in the areas affected by hip surgery. The provision of cold therapy is particularly desirable. FIG. 12 depicts thermal pack 90. In the example of FIG. 12, thermal transfer pack 90 includes two liquid-impermeable layers joined together along a sealed perimeter 92 to create an enclosed volume. Valve 96 provides a controlled passage from the exterior to the interior. The interior contains a heat transfer medium. This is preferably a hydrating liquid consisting of a solution of water and a humectant selected from the group consisting of propylene glycol, ethylene glycol, glycerin, dimethyl sulfoxide, dimethyl formamide, and combinations thereof.

When this substance transitions to a solid it expands to a form that is similar to packed snow or crushed ice. As a result the cold pack remains soft and malleable even when in a frozen state. Air is admitted to the interior through valve 96 during the freezing process. When the medium melts valve 96 allows air out of the enclosed interior but not the liquid medium.

Hook panels 94 are provided to attach thermal transfer pack 90 to the inward facing surface of the present invention—as will be explained. Each pack has an inward facing surface and an outward facing surface. The outward facing surface includes the hook panels. The inward facing surface is intended to face the user when the pack is in use. The inward facing surface preferably includes a layer of cover material. The cover material is preferably a soft and compliant material that may be comfortably worn against the user's thin clothing (such as a T-shirt) or even directly against the user's skin. This material preferably wicks moisture away from the user as well. The cover material may be bonded to the thermal transfer pack by any suitable method—including adhesives or stitching. It is preferable for the side facing the user to have no exposed discontinuities as these may be irritating.

The cooling media within the pack may be subdivided into many small bags ("sub-bags") contained within the larger volume. These "sub-bags" may be small—on the order of 1 to 2 inches square. The cooling media contained within the overall interior of thermal pack 90 is preferably a substance such as shown in U.S. Pat. No. 5,800,491 to Kolen and Nebolon. This substance forms an organized crystalline solid with a consistency similar to snow. Even as a solid, it remains soft and malleable. However, the substance such as disclosed in the '491 patent does not absorb as much energy during the transition from a solid to a liquid as pure water. Water can absorb more thermal energy, yet water has an undesirable property in that it solidifies into a hard mass (ice). If thermal pack 90 were simply filled with water and frozen, the result would be a rigid object that would be quite uncomfortable to wear. It is therefore desirable to provide a duplex construction of a large bag with many smaller sub-bags. The sub-bags contain pure water, or nearly so. The volume within the thermal pack as a whole but outside the sub-bags contains a substance such as shown in Kolen and Nebolon. Readers wishing to know more detail concerning this structure are referred to U.S. patent application Ser. No. 15/645,206. U.S. patent application Ser. No. 15/645,206 is hereby incorporated by reference.

The use of sub-bags within the larger volume provides the advantageous latent heat of water while retaining most of the beneficial aspects of the substance described in the '491 patent. Each sub-bag is filled with water. Small amounts of other substances may be present as well, but water is by far the main constituent. The volume contained within the interior of the thermal pack but outside the sub-bags is filled with a substance that creates a snow-like solid (such as described in the '491 patent). The result is an advantageous combination of features. Each individual sub-bag freezes into a hard object (containing ice). The surrounding volume freezes into a malleable snow-like substance. The sub-bags are relatively small—preferably less than 3 cm on a side and even more preferably less than 2 cm on a side. Thus, the overall thermal pack can still bend and flex because the sub-bags can move about within the snow-like frozen substance surrounding them. The user employs the composite thermal pack in the same way. However, the composite nature of the bag allows a greater absorption of thermal energy for the same unit volume.

Figure 13:
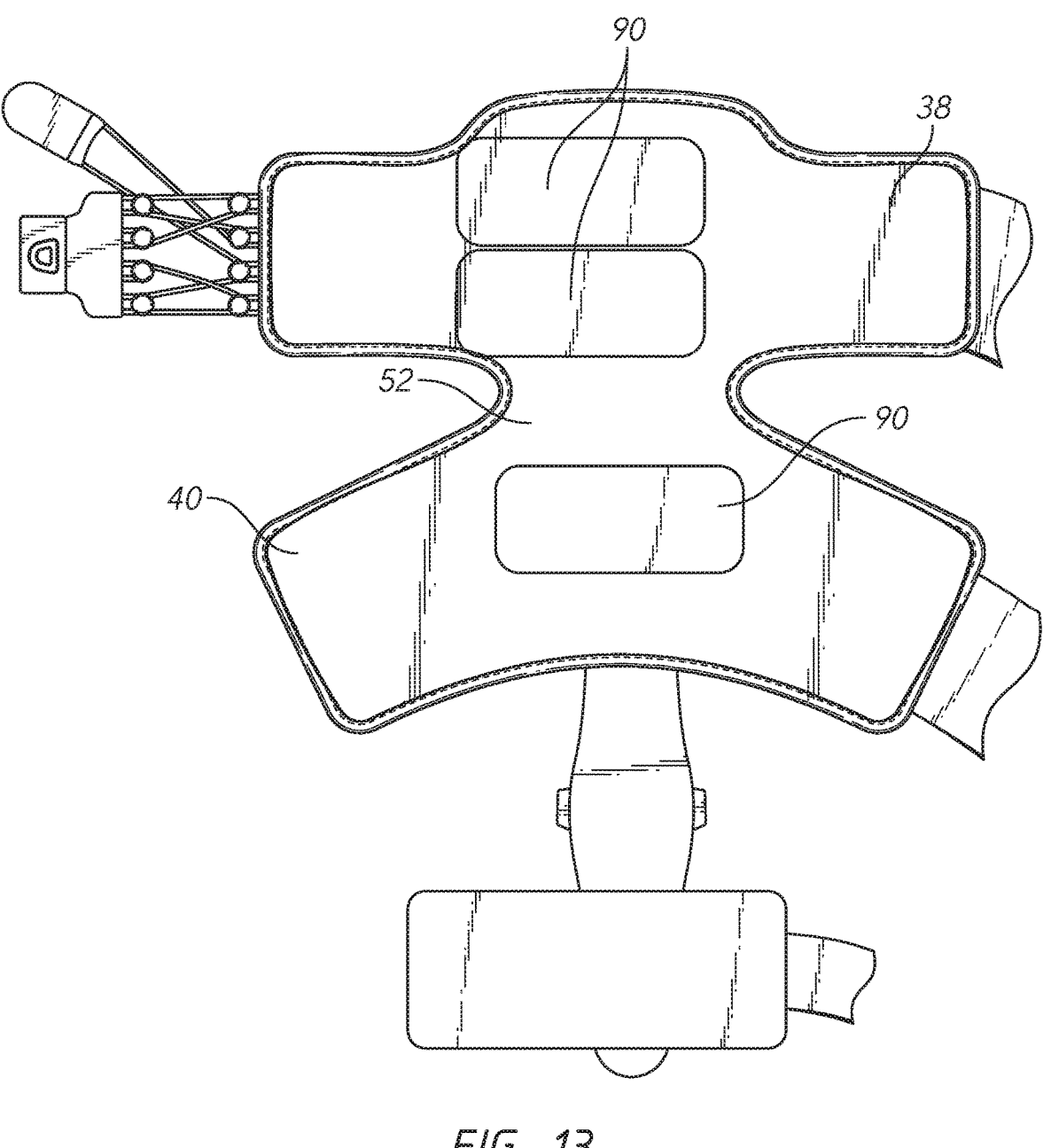
FIG. 13 is an elevation view, showing the inward facing side of the assembled orthotic.

In some versions of the composite thermal transfer bag the sub-bags or outer bag can include a thermochromatic material. This material changes color when the media freezes—thereby clearly indicating to the user whether all the sub-bags are fully transitioned to a solid. In some versions a thermochromatic ink may be added to the water within the sub-bags. In other versions, the thermochromatic material will be a film added to the sub-bags, the overall bag, or both. FIG. 13 shows an exemplary application of multiple thermal packs to the inventive orthotic. FIG. 13 depicts the inward-facing side of the orthotic ("inward" meaning the side intended to face the user). The inward facing surface of waist panel 38, central web 52, and thigh panel 40 are covered with loop material. Thermal packs 90 are positioned as shown. Each thermal pack is then attached to the inward facing surface of the panel assembly by pressing the hook panels on the thermal packs against the loop covering on the panel assembly. The resulting engagement holds the thermal packs in place, even when the orthotic is lifted and manipulated as part of the process of placing the orthotic on the user.

On the other hand, if a user wishes to move one of the thermal packs, it is a simple matter of peeling it off and sticking it in a new location. This will be done regularly, as the thermal packs must be swapped for replacement packs every few hours. It is common for a user to keep one set of packs in the freezer while a second set of packs is being worn. Once the set of packs being worn has transitioned back to a liquid state, the user swaps the packs for the set in the freezer. It is desirable to make the orthotic easy to remove and reattach. Many features are provided on the orthotic to accommodate this desire.

FIGS. 14-17 illustrate an additional embodiment of the inventive orthotic. It is desirable with the use of thermal packs to provide additional inward compressive force in order to force the packs tightly against the body. This inward compression causes the packs to conform to the user's exterior surface and enhance heat transfer.

Figure 14:
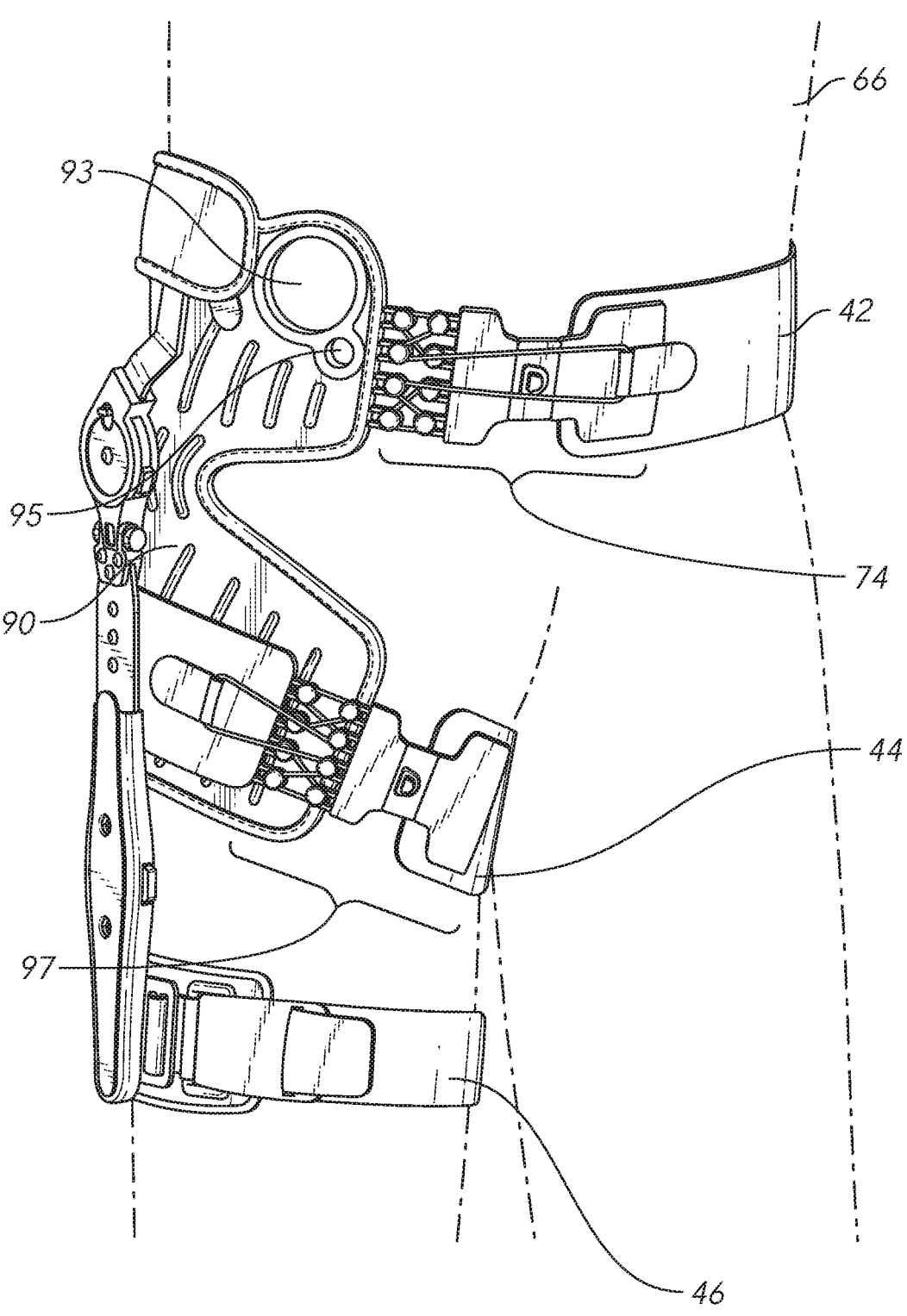
FIG. 14 is a perspective view, showing the inventive orthotic in an installed state.

FIG. 14 shows the additional embodiment being worn by a user. The panel assembly in this version is equipped with an internal air bladder. Squeeze bulb 93 is used to selectively inflate this air bladder. The squeeze bulb is connected to the air bladder by a one-way valve. Every time the user squeezes the squeeze bulb the pressure within the air bladder increases. If the user wishes to decrease the pressure within the air bladder, he or she presses release 95.

In operation the orthotic is donned (usually with a thermal pack or packs in place). The user then adjusts the waist strap, upper thigh strap, and lower thigh strap to provide a good fit. The user then squeezes squeeze bulb 93 until the desired level of compression is reached. When the time comes to remove the orthotic, the user presses release 95 and then unlatches the three straps (waist, upper thigh, and lower thigh).

Figure 15:
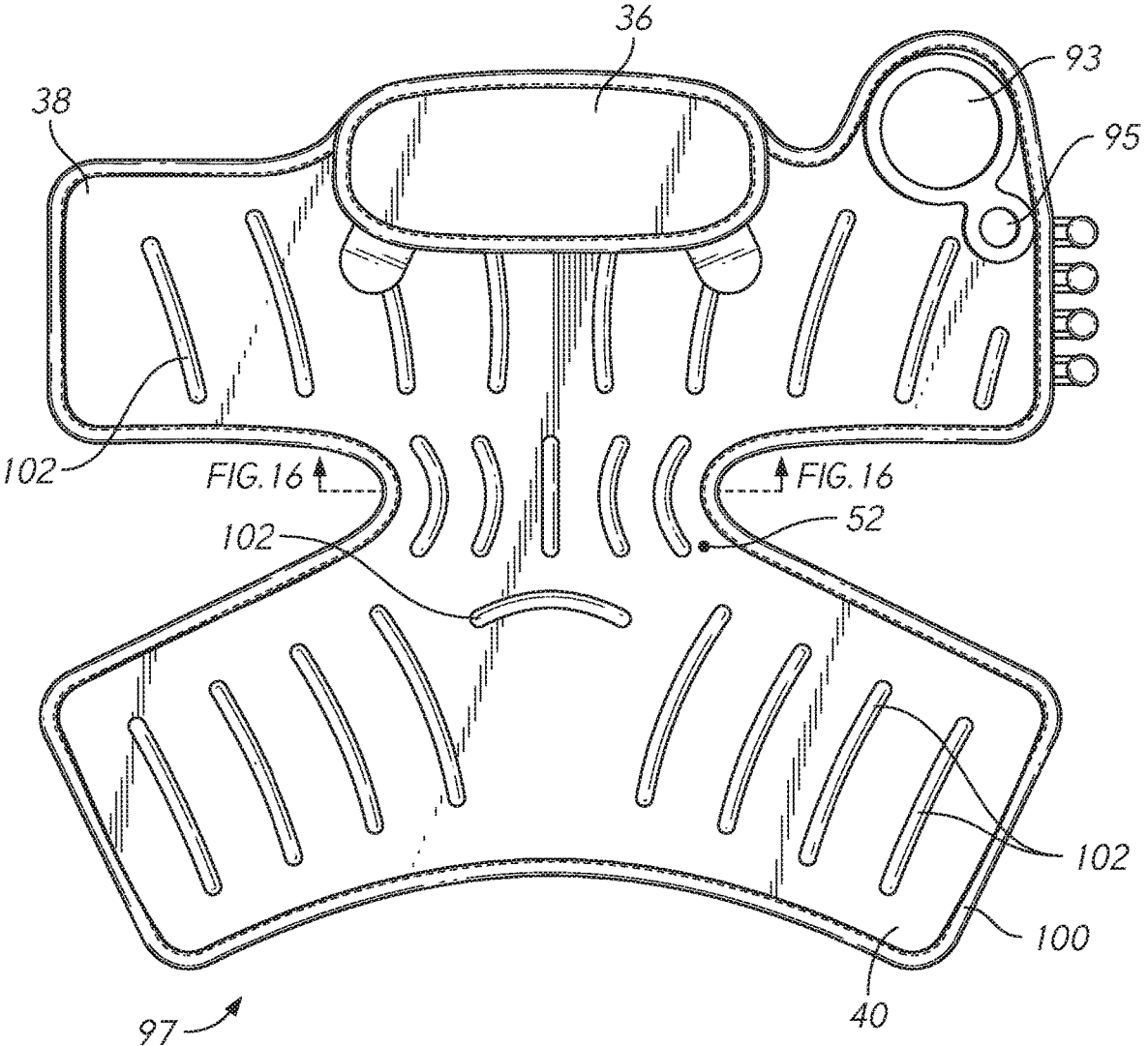
FIG. 15 is a plan view, showing a completed panel assembly for a pneumatic embodiment of the invention.

FIG. 15 shows the panel assembly as modified by the inclusion of the internal air bladder. The panel assembly is designated as pneumatic panel assembly 97. Its structure is similar to the panel assembly used in the embodiment of FIG. 4. Squeeze bulb 93 and release 95 are added in a convenient location. In addition, numerous seams 102 are added to organize the internal air bladder in a desired fashion. These seams subdivide the air bladder into a series of semi-tubular chambers, resulting in a structure similar to that of an "air mattress."

Figure 16:
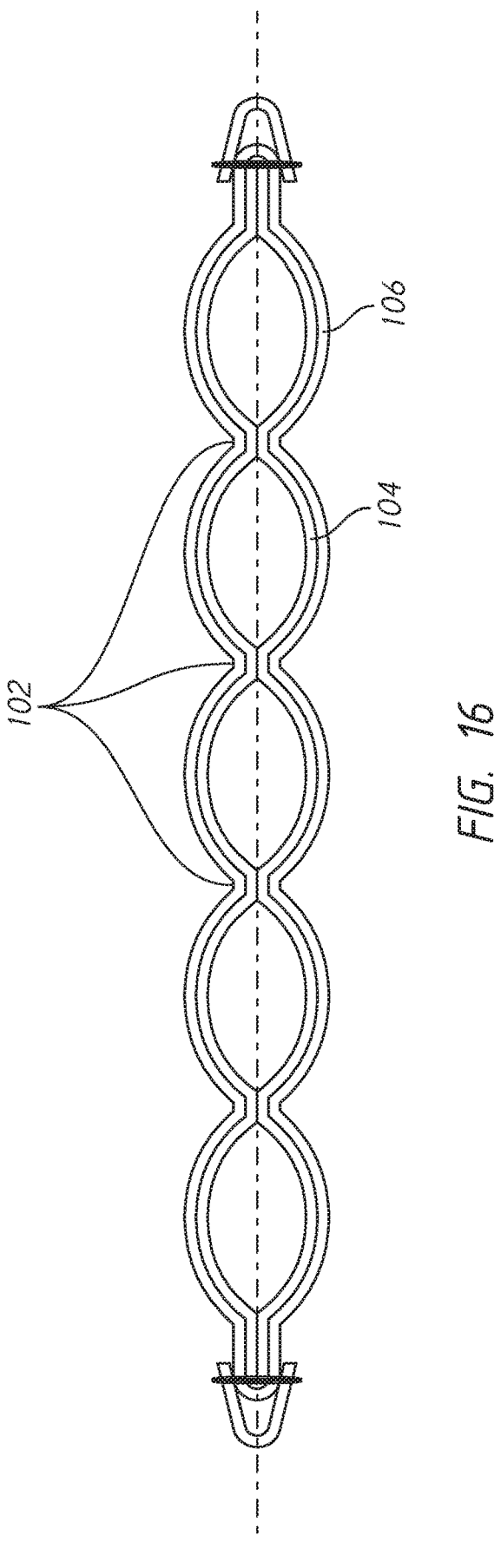
FIG. 16 is a sectional elevation view through the panel assembly of FIG. 15.

FIG. 16 shows a sectional elevation view taken through the region of central web 52. Air bladder 104 is the innermost layer. This is covered by a fabric outer layer 106. Edge band 100 is sewn around the perimeter of the panel assembly. The air bladder is sealed around the outer perimeter. The air bladder is also sealed along seams 102. These can be created by pressing the material along the seam together and fusing the four layers where they contact (such as by "heat staking" or ultrasonic welding). The user wishing to know more about the details of constructing the air bladder and the seams is referred to U.S. Pat. No. 9,750,630, which is hereby incorporated by reference.

Returning to FIG. 14, the operation of removing the inventive orthotic will be described in detail. The user starts by pressing release 95 to deflate the air bladder. The user next pulls free adjustment tab 56, adjustment tab 57, and hook panel 76 (see FIG. 7). The user then presses the release button 70 in each of the adjustable couplings 74, 97. The orthotic may then be pulled free and laid on a surface with its inward facing side facing upward—such as depicted in FIG. 13. The user then pulls the thermal packs 90 free and replaces them with a fresh set. The orthotic is then donned as described previously.

As mentioned previously, the inventive orthotic has two main components (the brace assembly and the panel assembly). It is possible to separate the brace assembly so that the panel assembly can be used without the brace assembly. As a patient progresses after surgery, the use of the rigid brace assembly may no longer be needed (such as when a restriction on the range of motion is no longer needed). However, these patients may desire to continue using thermal packs as part of rehabilitation.

Looking again at FIG. 8, the process of removing the brace assembly will be described. In the example shown, the user starts by pulling the two hook panels 84 free of the loop covering on thigh panel 40. The user then lifts the brace assembly up and away from thigh panel 40. The user then pulls the two hook panels 98 free from waist panel 38 and slides upper plate 22 down and out of pocket 82.

At this point the brace assembly is free from the panel assembly. However, the user will recall that upper thigh strap 44 is connected to lower link 26 of the brace assembly. It is desirable to use the upper thigh strap with the panel assembly, so it must first be detached from the brace assembly. If detachable fasteners are used to attach the upper thigh strap to lower link 26 then these are simply detached.

If stitching is used for the attachment then the stitching will have to be cut. Whatever approach is taken, upper thigh strap 44 is preferably separated from the brace assembly. Once separated, the upper thigh strap can be connected to thigh panel 40 by pressing the two hook panels 84 against the loop covering on the exterior of the thigh panel. The panel assembly can then be used as a compressive orthotic with waist strap 42 and upper thigh strap 44 (but without lower thigh strap 46).

Figure 17:
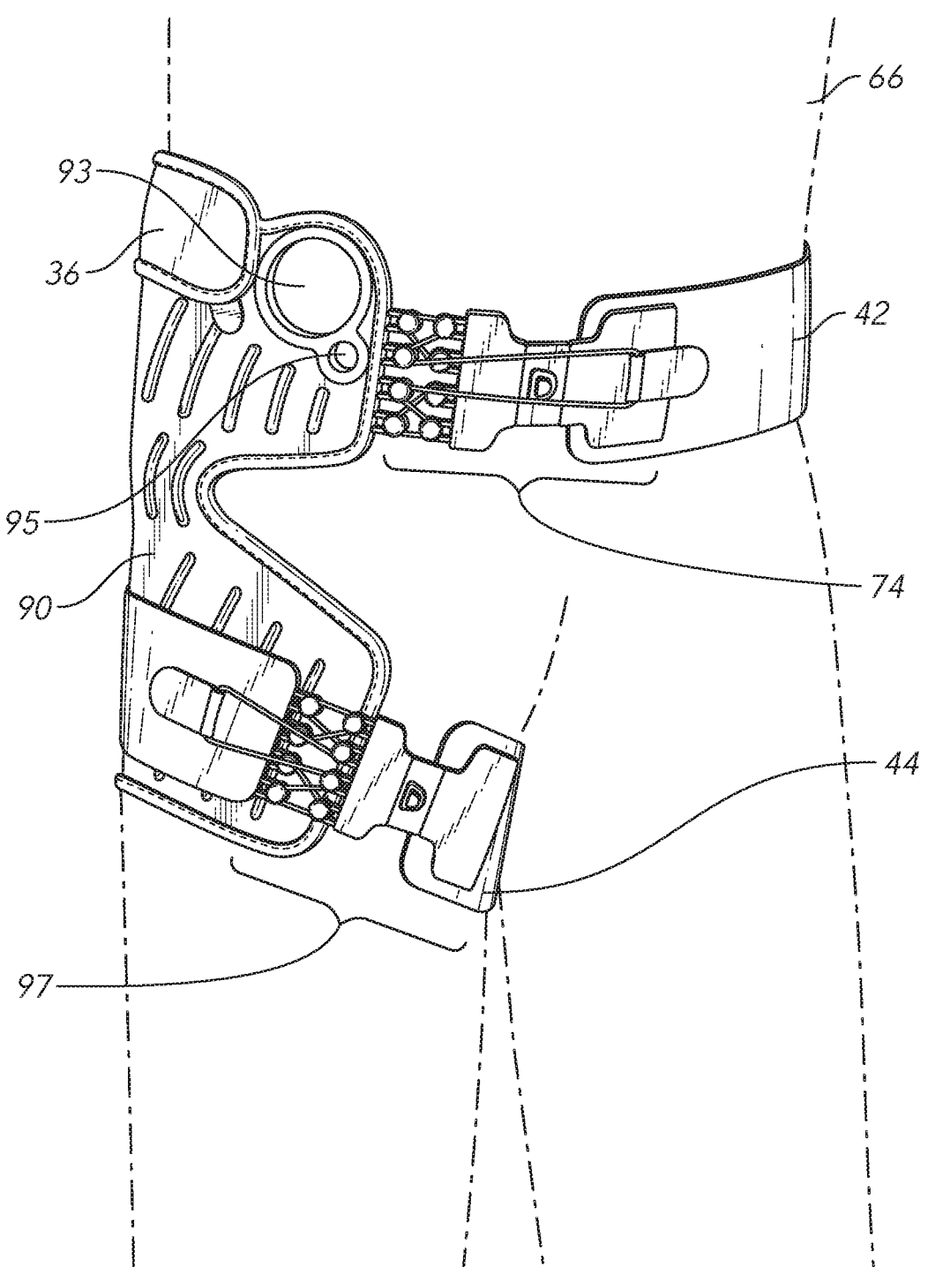
FIG. 17 is a perspective view, showing a user wearing the inventive orthotic with the brace assembly omitted.

FIG. 17 shows the orthotic in this state applied to user 66. One or more thermal packs are typically attached before the orthotic is donned. Waist strap 42 can be tightened to a desired degree using adjustable coupling 74. Likewise, upper thigh strap 44 can be tightened to a desired degree using adjustable coupling 97. The user then presses squeeze bulb 93 to inflate the internal air bladder to a desired pressure. The orthotic may be removed as desired for replacement of the thermal packs.

In some applications it is desirable to repetitively remove and replace the brace assembly. For example, the presence of the brace assembly may be desirable for exercise periods but undesirable for rest periods. Accordingly, it is beneficial to provide embodiments in which the brace assembly can be easily removed from the panel assembly (the soft portions of the brace) and subsequently reattached.

Figure 18:
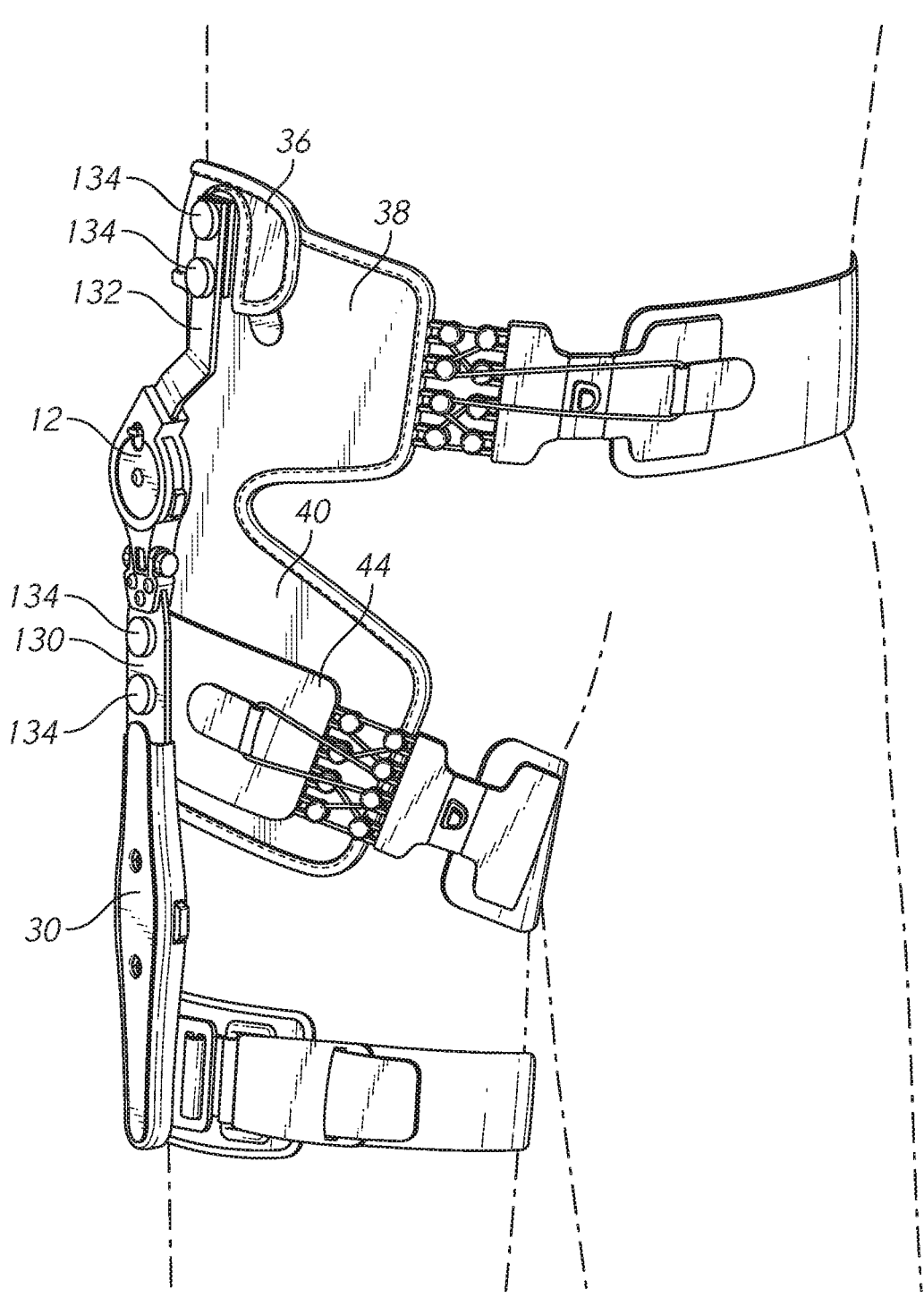
FIG. 18 is a perspective view, showing an embodiment of the inventive orthotic with a removable brace assembly.

FIG. 18 shows a first embodiment of the inventive orthotic with the easily removable brace assembly. The removable brace is similar to the version shown in FIG. 1. Upper link 132 is pivotally connected to lower link 130 by pivot mechanism 12. Slide body 30 is slidably connected to lower link 130. In this detachable embodiment, however, four fasteners 134 connect the brace assembly to the panel assembly. Two fasteners 134 connect lower link 130 to a lower plate connected to thigh panel 40. Two additional fasteners 134 connect upper link 132 to an upper plate contained within upper plate cover 36.

Fasteners 134 may assume a wide variety of forms, including screws, quarter-turn fasteners, bayonet-lug fasteners, and sliding links. The fasteners depicted in FIG. 18 are metal machine screws with an enlarged plastic head. The enlarged head facilitates gripping and removal without the need for a separate tool.

Figure 19:
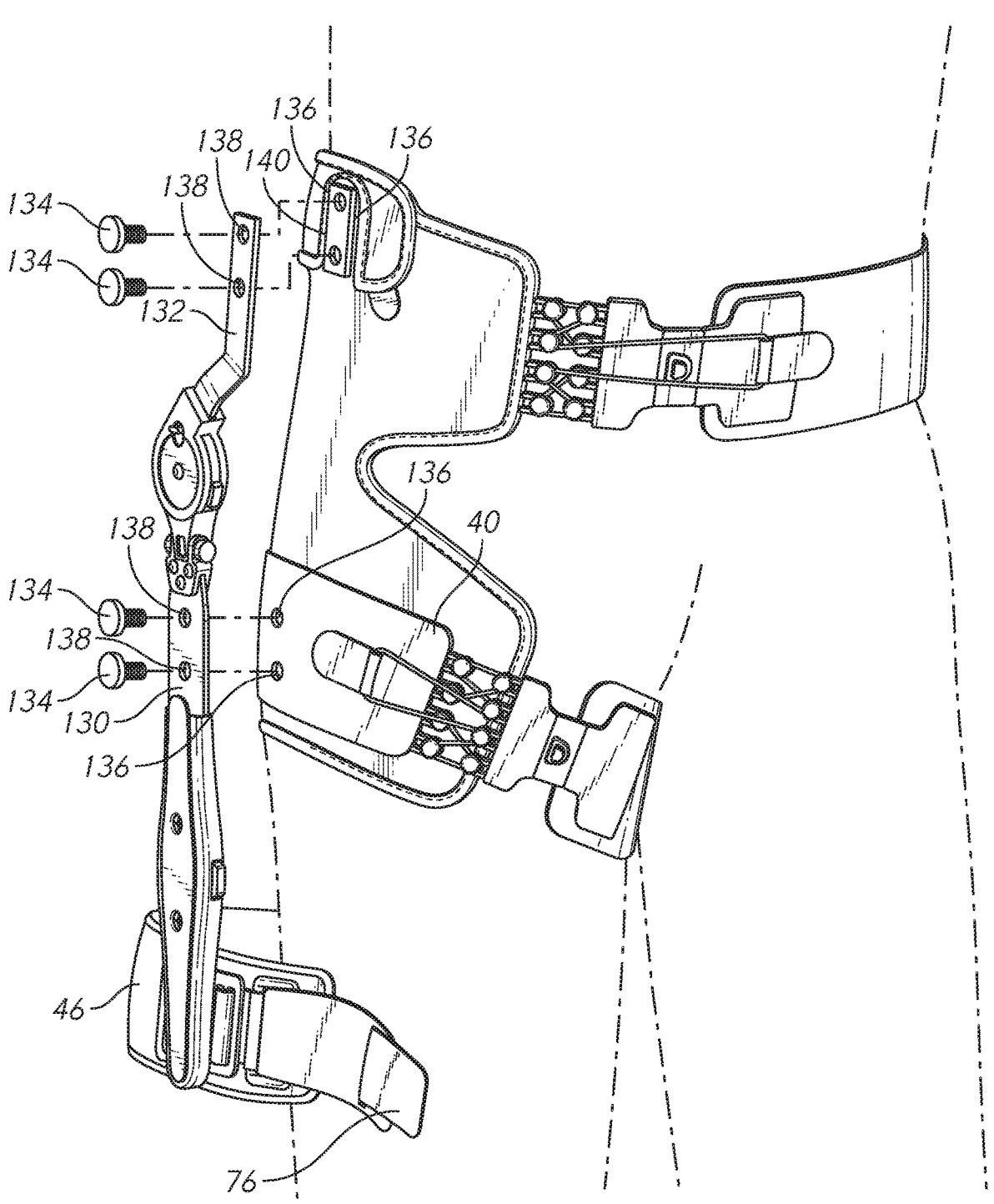
FIG. 19 is a perspective view, showing the assembly of FIG. 18 with the brace assembly removed.

FIG. 19 shows the same assembly in an exploded state. Fasteners 134 have been unscrewed and pulled free of holes 138 in upper link 132 and lower link 130. Hook panel 76 has been pulled free and lower thigh strap 46 has been removed from the leg. The entire brace assembly has thus been pulled free from the panel assembly (the soft portion of the inventive orthotic). Two captive nuts 136 are retained in offset bracket 140 near the top of the waist panel. Two additional captive nuts 136 are retained in the vicinity of thigh panel 40. The upper two captive nuts receive the fasteners for upper link 132. The lower two captive nuts receive the fasteners for lower link 130. The reader will thereby perceive that a user can easily reattach the brace assembly by inserting each fastener 134 through a hole 138 and into a captive nut 136.

FIGS. 20-24 provide additional details regarding exemplary hardware that is used to attach the removable brace assembly to the soft portions of the orthotic. Returning briefly to FIG. 1, the reader will recall that the non-removable version of the brace assembly includes upper plate 22 and lower plate 28. Looking now at FIG. 8, the reader will recall that lower plate 28 is typically secured to thigh panel 40 and upper plate 22 is typically secured to waist panel 38. The embodiments incorporating the removable brace assembly preferably still provide a lower plate attached to the thigh panel and an upper plate attached to the waist panel. It is preferable for the two plates 22, 28 to remain with the panel assembly when the brace assembly is removed.

Figure 20:
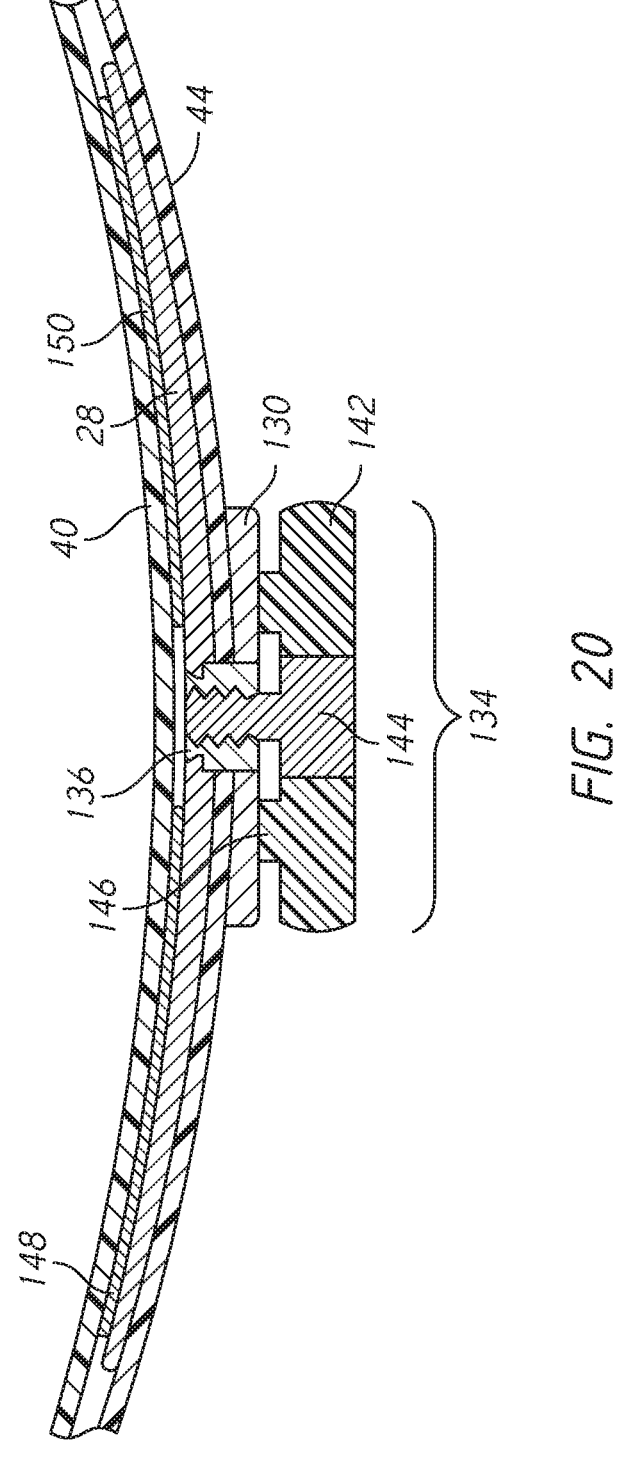
FIG. 20 is a detailed sectional view, showing one approach to detachably connecting the removable brace assembly.

FIG. 20 provides a detailed sectional view through thigh panel 40 with the removable brace assembly installed. The section plane is taken through the central bore of one of the captive nuts 136. As for the non-removable examples, lower panel 28 is secured between thigh panel 40 and upper thigh strap 44. Hook panels 148, 150 on the inward-facing side of lower panel 28 engage the outward-facing hook-compatible surface on thigh panel 40.

Captive nut 136 is secured to lower panel 28. In this example the lower panel is made of metal—such as soft aluminum. Captive nut 136 is swaged into a hole in the metal and thereby secured. Many different types of captive nuts can be used. A good example is a "PEM" nut as supplied by Penn Engineering and Manufacturing of Danboro, Pennsylvania, U.S.A.

The exemplary captive nut shown has a threaded internal bore and a cylindrical exterior that extends outward beyond the outward facing surface of lower panel 28 and beyond upper thigh strap 44 (A clearance hole is provided through the upper thigh strap).

Lower link 130 includes two holes 138 (seen clearly in FIG. 19). Each hole is sized to be a close sliding fit over the protruding cylindrical exterior of captive nut 136. FIG. 20 shows lower link 130 secured to captive nut 136 by sliding a hole 138 in lower link 130 over the cylindrical exterior of captive nut 136. Fastener 134 is then used to clamp lower link 130 firmly in place.

In the example shown, fastener 134 has a metal insert 144 and an overmolded polymer grip disk 142. Insert 144 includes a threaded protrusion that threads into captive nut 136. Grip disk 142 is preferably made large enough for a user to manually grasp and tighten/loosen fastener 134 without the need for a tool.

Fastener 134 includes an annular contact pad 146. As the user grasps and turns grip disk 142, annular contact pad 46 presses against lower link (over a broad area) and urges it toward lower panel 28. The engagement shown in FIG. 20 is repeated for two locations (the two holes 138 in lower link 130). Lower link 130 is thereby positively located by the engagement of the two holes 138 and captive nuts 136. Lower link 130 is held in place via the compression provided by the two fasteners 134.

In the example of FIG. 20, grip disk 142 is bonded to insert 144 via an overmolding process. The two components may be bonded by other means—such as through the use of an adhesive. Of course, one could also make the two components 142, 144 as a single integral unit.

The junction shown in FIG. 20 can also be used for the two fasteners securing upper link 132. However, the reader will recall that the upper link and upper plate optionally include a sliding joint between the upper link and the upper plate. An example of this sliding joint is shown in FIGS. 3B and 3C. It is preferable for the implementation of the detachable brace assembly to accommodate such a sliding joint.

Looking against at FIG. 19, the reader will note that the captive nuts 136 used to secure upper link 132 are not directly attached to the upper plate. Rather—in the example shown in the view—they are attached to offset bracket 140. A section view through one of the captive nuts 136 in offset bracket 140 is shown in FIG. 21.

Figure 21:
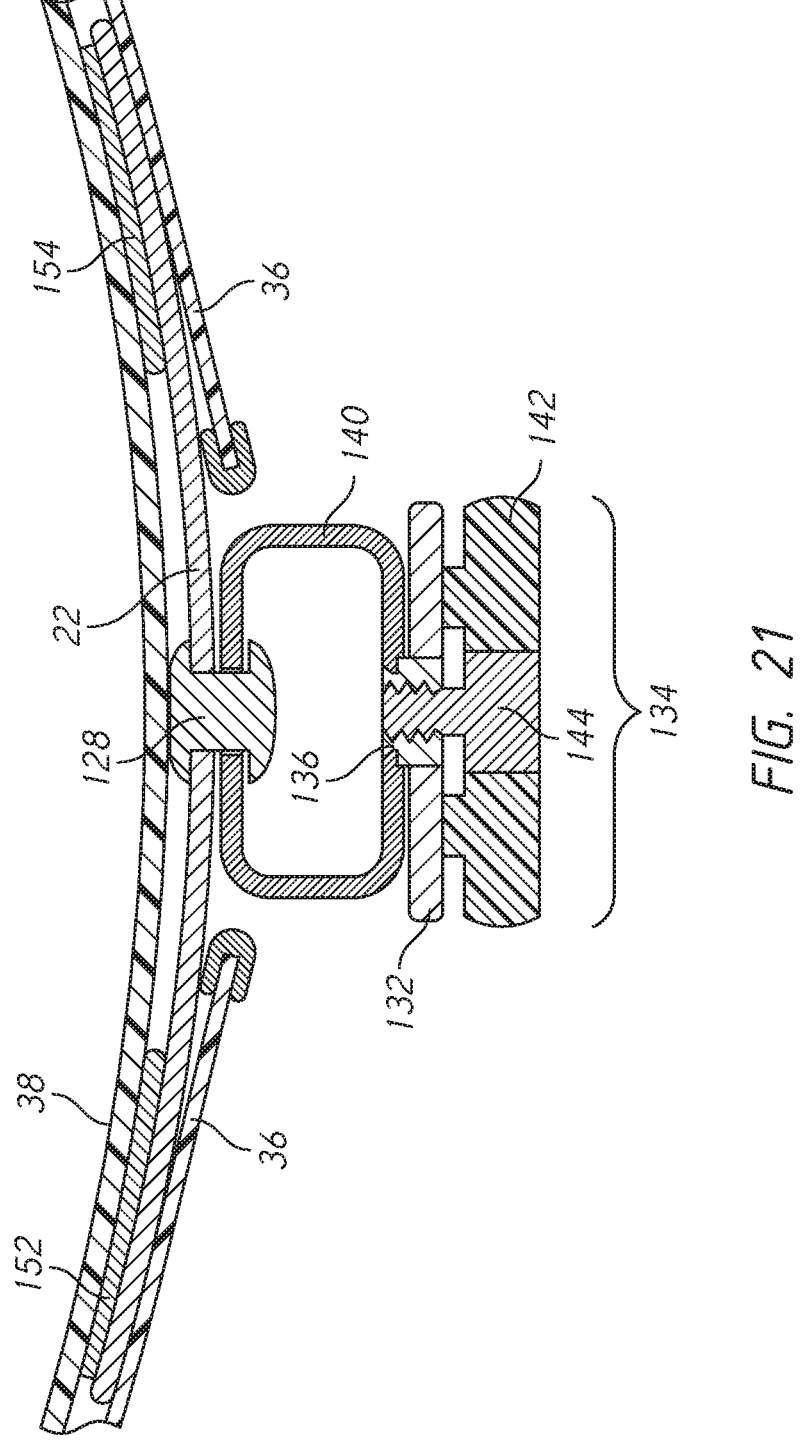
FIG. 21 is a detailed sectional view, showing another approach to detachably connecting the removable brace assembly.

In the example of FIG. 21, upper plate 22 is secured between waist panel 38 and upper plate cover 36. Hook panels 152, 154 secure the inward-facing surface of upper plate 22 to the outward-facing hook-compatible surface of waist panel 38.

Offset bracket 140 is slidably secured to upper plate 22 by slide rivet 128 (The operation of the slide rivet has previously been explained). In this example offset bracket 140 is made from a piece of hollow rectangular tubing (The use of the word "tubing" in the descriptive term "rectangular tubing" may seem to be a contradiction in terms, but it is the standard term used for hollow thin-walled metal stock). Captive nut 136 is swaged into the outward-facing side of offset bracket 140. The rivet nut contains a female threaded bore. It also contains a cylindrical exterior that protrudes outward well beyond the outward-facing surface of offset bracket 140. One of the holes 138 in upper link 132 is sized to be a close sliding fit over the cylindrical exterior of the rivet nut—as shown. Once upper link 132 is in place, fastener 134 is threaded into rivet nut 136. Upper link 132 is thereby secured against offset bracket 140. However, the sliding connection is preserved (via the fact that offset bracket 140 can slide with respect to upper plate 22). Additional holes can be provided in the offset bracket to permit the introduction of a bucking bar or squeeze jaw that may be needed to install the slide rivets.

The lateral offset (with respect to the hip) provided by offset bracket 140—if sized correctly—can eliminate the need for an offsetting "dogleg" in upper link 132. Returning to FIG. 19, the reader will note that while upper link 132 still has an angular dogleg, it lacks a lateral dogleg (compare to the version shown in FIG. 7).

Figure 22:
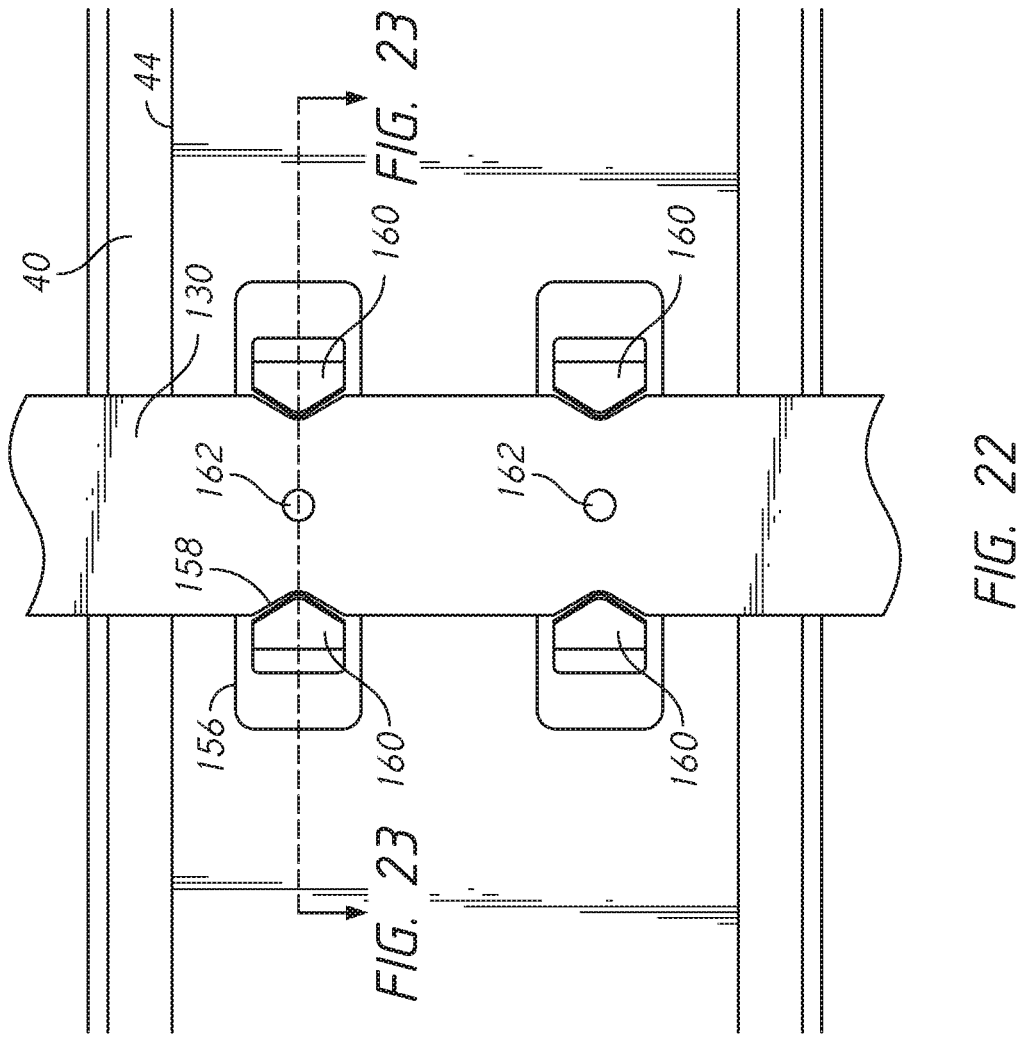
FIG. 22 is a detailed elevation view, showing another approach to detachably connecting the removable brace assembly.
Figure 23:
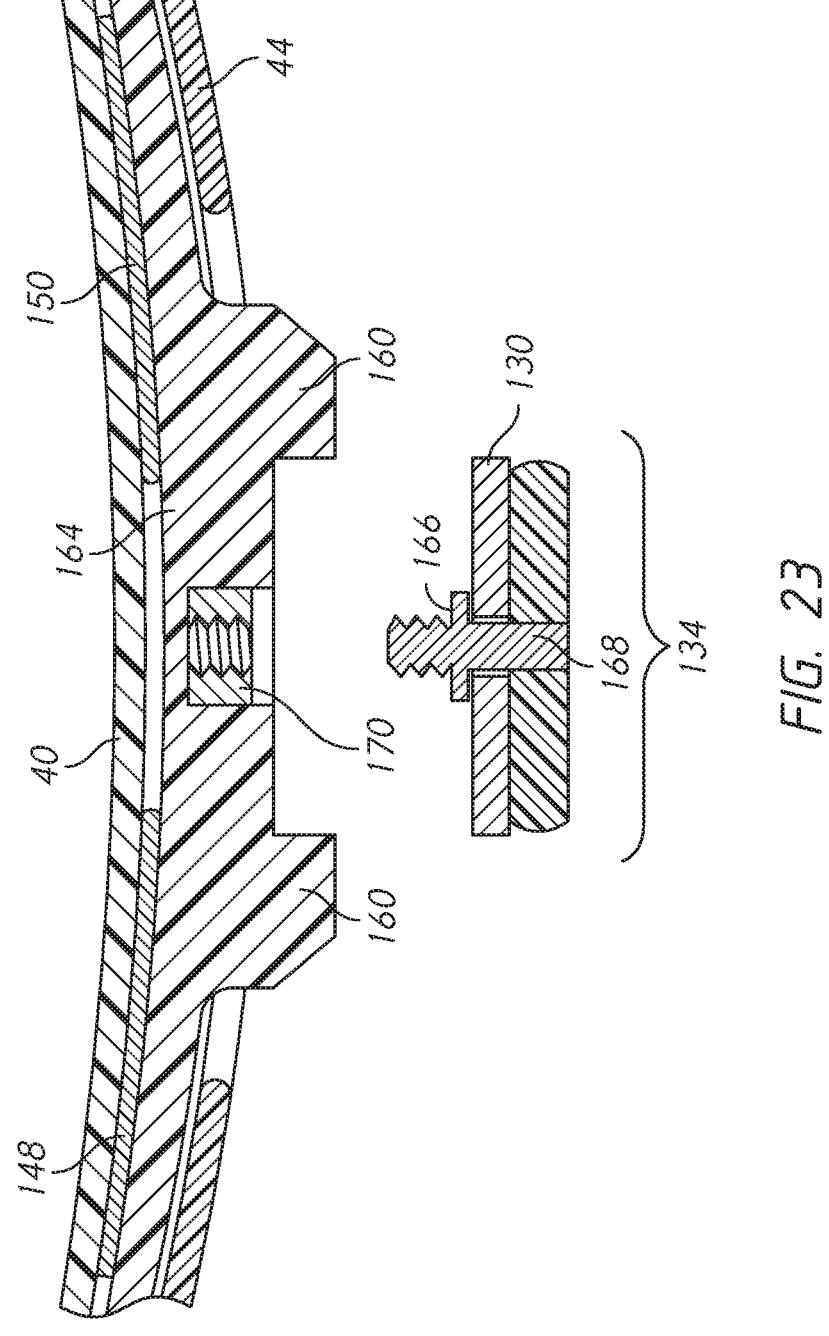
FIG. 23 is a detailed sectional view, showing another approach to detachably connecting the removable brace assembly.
Figure 24:
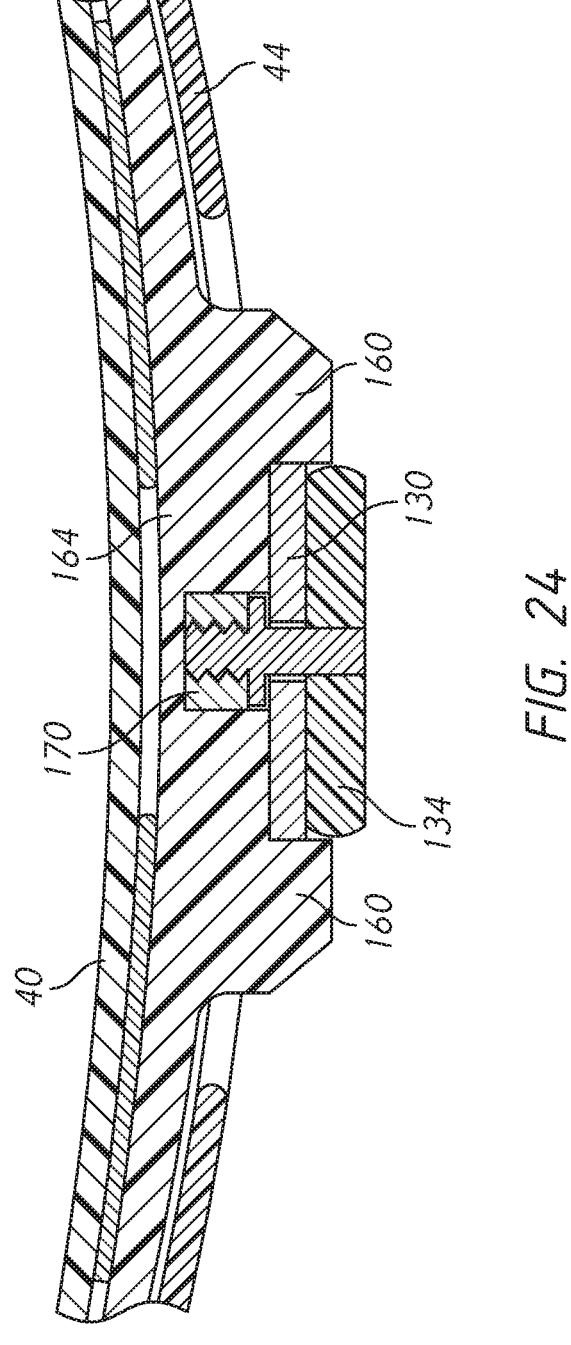
FIG. 24 is a detailed sectional view, showing the embodiment of FIG. 23 in an assembled state.

It is possible to provide a molded plastic embodiment for the panels 22, 28. FIGS. 22-24 illustrate this embodiment. FIG. 22 shows an elevation view of lower link 130 in the vicinity of upper thigh strap 44. A polymer lower plate is contained between upper thigh strap 44 and thigh panel 44. Two reliefs 156 are provided in upper thigh strap 44 so that portions of the polymer lower plate can protrude outward. These portions—prongs 160—include inward-facing points. Lower link 130 includes four lateral notches 158 configured to receive these inward-facing points of prongs 160 as shown. The engagement of prongs 160 and notches 158 locates lower link 130 with respect to the polymer lower plate. Two holes 162 are also provided in lower link 130 to receive fasteners.

In FIG. 22, the section plane for the sectional view of FIG. 23 is "called out." FIG. 23 shows a sectional view with lower link 130 being separated from the panel assembly. Polymer lower plate 164 is secured between thigh panel 40 and upper thigh strap 44. Hook panels 148, 150 on the inward-facing side of the polymer lower plate engage the hook-compatible outward-facing surface of thigh panel 40.

The polymer lower plate is curved to provide a good fit against the user. Prongs 160 extend outward as shown. Captive nut 170 in this example is a molding insert. Its outer cylindrical surface is knurled. It is placed in the mold and thermoplastic material is then shot around the insert. Its knurled exterior surface locks the insert to the polymer lower plate. Captive nut 170 includes a female-threaded central bore, as shown.

Lower link 130 is shown in the detached position. The section is takes through the middle of a pair of notches 158 in lower link 130 (The notches are shown in FIG. 22). The reader will note how the width of the lower link between the two notches can fit between the two prongs 160.

It is desirable for fasteners 134 to remain attached to the brace assembly when the brace assembly is removed, in order to prevent their loss. In the example of FIG. 23, insert

168 includes a retaining ring 166 as shown. The retaining ring lies on the same side of the insert as the threaded shaft that is configured to thread into captive nut 170. The opposite end of insert 168 is bonded to a large polymer grip disk. The bonding between insert 168 and the grip disk can be done via an overmolding process or an adhesive bonding process.

Another exemplary approach is to screw the insert into an ultrasonic welding machine so that the insert becomes a "horn" for ultrasonically melting a thermoplastic. The insert is places through the holes 162 in lower link 130. The outward portion of insert 168 is placed at the start of a pilot hole molded into the grip disk. The ultrasonic welding machine is then activated and the insert is driven into the grip disk and thereby bonded to the grip disk.

It is also possible to create retaining ring 166 by providing a groove in the exterior of the insert and installing a circlip or e-clip. Whatever method is used, the reader will appreciate that fastener 134 remains attached to the brace assembly when the brace assembly is detached from the panel assembly. Fastener 134 remains free to rotate with respect to lower link 130, however. The approach shown in FIG. 23 can also be applied to the embodiment of FIG. 18-21.

FIG. 24 shows the same sectional view as FIG. 23—but after fastener 134 has been threaded into captive nut 170 and tightened. The reader will observe how lower link 130 has been drawn securely between the two prongs 160 and thereby secured.

A similar configuration can be used for a polymer upper plate. Looking back at FIG. 21, those skilled in the art will know that a polymer version of upper plate 22 and offset bracket 140 can be provided. The use of a molded polymer would also allow the creation of a sliding connection without the need for a separate slide rivet.

The features thus described can be combined and altered in many ways. Exemplary modifications include:

1. Attaching the detachable brace assembly to the panel assembly using hook-and-loop fasteners;
2. Employing fasteners 134 to connect the brace assembly to thigh panel 40 but using the engagement of upper plate 22 and upper plate cover 36 (as depicted in FIG. 8) to provide the detachable connection for the upper link.
3. Providing a detachment system where the plates stay with the brace assembly.
4. Providing a lanyard connecting each fastener to the brace assembly so that loose fasteners are not lost.
5. Providing a storage pocket for the fasteners on the panel assembly.

Although the preceding descriptions present considerable detail they should be properly viewed as illustrating embodiments of the present invention rather than limiting the scope of the invention. Many more embodiments following the same principles will occur to those skilled in the art. Accordingly, the scope of the invention should be fixed by the following claims rather than by the examples given.

The invention claimed is:

1. A hip orthotic configured to attach to a user's lateral waist, hip, and lateral thigh, comprising:
   (a) a waist panel configured to lie over said user's lateral waist, including,
   (i) an upper plate,
   (ii) an offset bracket slidably connected to said upper plate,
   (iii) a first protrusion extending outward from said offset bracket, (iv) a second protrusion extending outward from said offset bracket, said second protrusion being offset from said first protrusion;

(b) a thigh panel configured to lie over said user's lateral thigh, including, (i) a lower plate, (ii) a third protrusion extending outward from said lower plate, (iii) a fourth protrusion extending outward from said lower plate, said fourth protrusion being offset from said third protrusion;

(c) a brace assembly, including, (i) an upper link, (ii) a lower link, (iii) a pivot mechanism between said upper link and said lower link;

(d) said upper link including a first hole, and a second hole offset from said first hole;

(e) said first and second holes being sized and positioned so that said first hole is a sliding fit over said first protrusion and said second hole is a sliding fit over said second protrusion, thereby positively locating said upper link with respect to said offset bracket when said first hole is slid over said first protrusion and said second hole is slid over said second protrusion;

(f) said lower link including a third hole, and a fourth hole laterally offset from said third hole;

(g) said third and fourth holes being sized and positioned so that said third hole is a sliding fit over said third protrusion and said fourth hole is a sliding fit over said fourth protrusion, thereby positively locating said lower link with respect to said lower plate when said third hole is slid over said third protrusion and said fourth hole is slid over said fourth protrusion;

(h) a first threaded hole proximate said first protrusion;

(i) a second threaded hole proximate said second protrusion;

(j) a third threaded hole proximate said third protrusion;

(k) a fourth threaded hole proximate said fourth protrusion;

(l) a first fastener passed through said first hole in said upper link and into said first threaded hole;

(m) a second fastener passed through said second hole in said upper link and into said second threaded hole;

(n) a third fastener passed through said third hole in said lower link and into said third threaded hole; and (o) a fourth fastener passed through said fourth hole in said lower link and into said fourth threaded hole.

2. The hip orthotic as recited in claim 1, comprising: (a) wherein said waist panel and said thigh panel both have an inward facing side with a loop covering; (b} a thermal transfer bag configured to attach to said loop covering, said thermal transfer bag including, (i) a sealed interior volume containing heat transfer media, (ii) an outward facing surface having a hook panel configured to engage said loop covering on said inward facing side of said waist and said thigh panel, and (iii) an inward facing surface covered in a soft and compliant fabric.

3. The hip orthotic as recited in claim 1, wherein each of said protrusions and said threaded holes are part of a captive nut.

4. The hip orthotic as recited in claim 1, wherein said third and fourth fasteners are configured to remain connected to said lower link when said lower link is removed from said lower plate.

5. The hip orthotic as recited in claim 1, wherein said first and second fasteners are configured to remain connected to said upper link when said upper link is removed.

6. A hip orthotic configured to attach to a user's lateral waist, hip, and lateral thigh, comprising:

(a) a waist panel configured to lie over said user's lateral waist, including, (i) an upper plate, (ii) an offset bracket connected to said upper plate, (iii) a first protrusion extending outward from said offset bracket, (iv) a second protrusion extending outward from said offset bracket, said second protrusion being offset from said first protrusion;

(b) a thigh panel configured to lie over said user's lateral thigh, including, (i) a lower plate, (ii) a third protrusion extending outward from said lower plate, (iii) a fourth protrusion extending outward from said lower plate, said fourth protrusion being offset from said third protrusion;

(c) a waist strap configured to encircle said waist of said user and secure said waist panel to said user;

(d) a thigh strap configured to encircle said thigh of said user and secure said thigh panel to said user;

(e) a brace assembly, including, (i) an upper link, (ii) a lower link, (iii) a pivot mechanism between said upper link and said lower link;

(f) said upper link including a first hole, and a second hole offset from said first hole;

(g) said first and second holes being sized and positioned so that said first hole is a sliding fit over said first protrusion and said second hole is a sliding fit over said second protrusion, thereby positively locating said upper link with respect to said offset bracket when said first hole is slid over said first protrusion and said second hole is slid over said second protrusion;

(h) said lower link including a third hole, and a fourth hole laterally offset from said third hole;

(i) said third and fourth holes being sized and positioned so that said third hole is a sliding fit over said third protrusion and said fourth hole is a sliding fit over said fourth protrusion, thereby positively locating said lower link with respect to said lower plate when said third hole is slid over said third protrusion and said fourth hole is slid over said fourth protrusion;

(j) a first threaded hole proximate said first protrusion;

(k) a second threaded hole proximate said second protrusion;

(l) a third threaded hole proximate said third protrusion;

(m) a fourth threaded hole proximate said fourth protrusion;

(n) a first fastener passed through said first hole in said upper link and into said first threaded hole;

(o) a second fastener passed through said second hole in said upper link and into said second threaded hole;

(p) a third fastener passed through said third hole in said lower link and into said third threaded hole; and (q) a fourth fastener passed through said fourth hole in said lower link and into said fourth threaded hole.

7. The hip orthotic as recited in claim 6, comprising: (a) wherein said panel assembly has an inward facing side with a loop covering; (b) a thermal transfer bag configured to attach to said loop covering on said inward facing side of said waist and said thigh panel, said thermal transfer bag including, 7) a sealed interior volume containing heat transfer media, (ii) an outward facing surface having a hook panel configured to engage said loop covering on said inward facing side of said waist and said thigh panel, and (iii) an inward facing surface covered in a soft and compliant fabric.

8. The hip orthotic as recited in claim 6, wherein: (a) an attachment between said upper link and said upper plate includes an offset bracket; and (b} said offset bracket includes an inward-facing side that is slidably connected to said upper panel.

9. The hip orthotic as recited in claim 6, wherein each of said protrusions and said threaded holes are part of a captive nut.

10. The hip orthotic as recited in claim 6, wherein said third and fourth fasteners are configured to remain connected to said lower link when said lower link is removed from said lower plate.

11. The hip orthotic as recited in claim 6, wherein said first and second fasteners are configured to remain connected to said upper link when said upper link is removed from said upper plate.

\*   \*   \*   \*   \*